US006515197B1

(12) United States Patent
Pulst et al.

(10) Patent No.: US 6,515,197 B1
(45) Date of Patent: Feb. 4, 2003

(54) TRANSGENIC MOUSE EXPRESSING A POLYNUCLEOTIDE ENCODING A HUMAN ATAXIN-2 POLYPEPTIDE

(75) Inventors: Stefan M. Pulst, Los Angeles, CA (US); Duong P. Huynh, Long Beach, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 09/648,281

(22) Filed: Aug. 24, 2000

(51) Int. Cl.[7] .................... A01K 67/027; A01K 67/033; G01N 33/00; C12Q 1/02; C12N 15/00
(52) U.S. Cl. .............................. 800/18; 860/8; 860/3; 435/29; 435/320.1; 435/354; 536/23.5
(58) Field of Search ........................... 800/3, 8, 12, 13, 800/18; 435/29, 325, 320.1, 354; 536/23.1, 24.1, 23.5

(56) References Cited

U.S. PATENT DOCUMENTS

| | | | |
|---|---|---|---|
| 5,175,384 A | 12/1992 | Krimpenfort et al. | 800/2 |
| 5,602,299 A | 2/1997 | Lazzarini | 800/2 |
| 5,604,131 A | * 2/1997 | Wadsworth et al. | 435/320.1 |
| 5,859,311 A | 1/1999 | Albers et al. | 800/2 |
| 6,037,521 A | 3/2000 | Sato et al. | 800/18 |
| 6,066,778 A | 5/2000 | Ginsburg et al. | 800/2 |

FOREIGN PATENT DOCUMENTS

| | | |
|---|---|---|
| WO | WO 97/42314 | 11/1997 |
| WO | WO 00/12710 | 3/2000 |

OTHER PUBLICATIONS

Ella Ioffe et al, WW6: An embryonic stem cell line with an inert genetic marker that can be traced in chimeras, vol. 92, pp. 7357–7361, Aug. 1995.*
Ram R. Shukla et al, Human Chromosome 6– and 11– Encoded Factors Support Human Immunodeficiency Virus Type 1 Rev Function in A9 Cells, Journal of Virology, Dec. 1996, pp. 9064–9068.*
Louis–Marie Houdebine, Production of Pharmaceutical proteins from transgenic animals, Journal of Biotechnology 34 1994 269–287.*
Chapman & Hall, Transgenic farm animals get off the ground, Transgenic Research 7, 73–75 1998.*
Linda J. Mullins et al, Perspectives Series: Molecular Medicine in genetically Engineered Animals, vol. 98, No. 11, Supplement 1996, S37–S40.*
R.J. Wall, Transgenic Livestock: Progress And Prospects For The Future, Theriogenelogy 45:57–68, 1996.*
John J. Mullins et al, Transgenesis in Nonmurine Species, Hypertension vol. 22, No. 4, Oct. 1993.*
Catherine A. Kappel et al, Regulating gene expression in transgenic animals, Current Opinion in Biotechnology 1992, 3:548–553.*
Curt D. Sigmund, Viewpoint: Are Studies in Genetically Altered Mice Out of Control? Arterioscler Thromb Vasc Biol. Jun. 2000.*
Ewan R. Cameron, Recent Advances in Transgenic Technology, Molecular Biotechnology vol. 7, 1997.*
Randall Wade Moreadith et al, Gene targeting in embryonic stem cells: the new physiology and metabolism, J Mol Med 1997, 75:208–216.*
Katja Prelle et al, Establishment of Pluripotent Cell Lines from Vertebrate Species—Present Status and Furure Propects, Cells Tissues Organs 1999; 165–220–236.*
Burright et al., "SCA1 Transgenic Mice: A Model for Neurodegeneration Caused by an Expanded CAG Trinucleotide Repeat," *Cell*, 82:937–948 (1995).
Cha et al., "Altered neurotransmitter receptor expression in transgenic mouse models of Huntington's disease," *Phil. Trans. R. Soc. Lond. B.*, 354:981–989 (1999).
Chai et al., "Evidence for proteasome involvement in polyglutamine disease: localization to nuclear inclusions in SCA3/MJD and suppression of polyglutamine aggregation in vitro," *Hum. Mol. Genet.*, 8:673–682 (1999).
Clark et al., "Purkinje Cell Expression of a Mutant Allele of SCA1 in Transgenic Mice Leads to Disparate Effects on Motor Behaviors, Followed by a Progressive Cerebellar Dysfunction and Histological Alterations," *J. Neurosci.*, 17:7385–7395 (1997).
Cummings et al., "Mutation of E6–AP ubiquitin ligase reduces nuclear inclusion frequency while accelerating polyglutamine–induced pathology in SCA1 mice," *Nueron*, 24:879–892 (1999).
Cummings et al., "Chaperone suppression of aggregation and altered subcellular proteasome localization imply protein misfolding in SCA1," *Nature Genet.*, 19:148–154 (1998).
David et al., "Cloning of the SCA7 gene reveals a highly unstable CAG repeat expansion," *Nature Genet.*, 17:65–70 (1997).
Davies et al., "Formation of neuronal intranuclear inclusions underlies the neurological dysfunction in mice transgenic for the HD mutation," *Cell*, 90:537–548 (1997).

(List continued on next page.)

*Primary Examiner*—Deborah Crouch
(74) *Attorney, Agent, or Firm*—Campbell & Flores LLP

(57) ABSTRACT

The invention provides a transgenic non-human mammal comprising nucleated cells containing a transgene encoding an ataxin-2 polypeptide comprising a polyglutamine tract. In particular, the transgenic-non-human mammal can be a mouse. The invention also provides methods of using a transgenic non-human mammal expressing SCA2 encoding an ataxin-2 polypeptide to identify a therapeutic agent for use in treating a neurodegenerative disease by administering a compound to a transgenic non-human mammal expressing SCA2 encoding an ataxin-2 polypeptide and screening the transgenic non-human mammal for an improved neurological response associated with a neurodegenerative phenotype of the transgenic non-human mammal, thereby identifying a therapeutic agent for use in treating the neurodegenerative disease.

39 Claims, 1 Drawing Sheet

OTHER PUBLICATIONS

GenBank: Accession No. U70323.

GenBank Accession No. U70670.

Gutekunst et al., "Nuclear and neuropil aggregates in Huntington's Disease: relationship to neuropathology," *J. Neurosci.*, 19:2522–2534 (1999).

Hodgson et al., "A YAC Mouse Model for Huntington's Disease with Full–Length Mutant Huntingtin, Cytoplasmic Toxicity, and Selective Striatal Neurodegeneration," *Neuron*, 23:181–192 (1999).

Hogan et al., *Manipulating the Mouse Embryo: A Laboratory Manual* Cold Spring Harbor Laboratory, (1986).

Holmberg et al., "Spinocerebellar ataxia type 7 (SCA7) : a neurodegenerative disorder with neuronal intranuclear inclusions," *Hum. Mol. Genet.*, 7:913–918 (1998).

Huntington's Disease Collaborative Research Group, "A Novel Gene Containing a Trinucleotide Repeat That Is Expanded and Unstable on Huntington's Disease Chromosomes," *Cell*, 72:971:983 (1993).

Huynh et al., "Expression of Ataxin–2 in Brains from Normal Individuals and Patients with Alzheimer's Disease and Spinocerebellar Ataxis 2," *Ann. Neurology*, 45:232–241 (1999).

Igarashi et al., "Suppression of aggregate formation and apoptosis by transglutaminase inhibitors in cells expressing truncated DRPLA protein with an expanded polyglutamine stretch," *Nature Genet.*, 18:111–117 (1998).

Ikeda et al., "Expanded polyglutamine in the Machado–Joseph disease protein induces cell death *in vitro* and *in vivo*," *Nature Genet.*, 13:196–202 (1999).

Imbert et al., "Cloning of the gene for spinocerebellar ataxia 2 reveals a locus with high sensitivity to expanded CAG/glutamine repeats," *Nature Genet.*, 14:285–291 (1996).

Ishikawa et al., "Abundant expression and cytoplasmic aggregation of α1A voltage–dependent calcium channel protein associated with neurodegeneration in spinocerebellar ataxia type 6," *Hum. Mol. Genet.*, 8:1185–1193 (1999).

Kawaguchi et al., "CAG expansions in a novel gene for Machado–Joseph disease at chromosome 14q32.1," *Nature Genet.*, 8:221–228 (1994).

Kim et al., "Mutant Huntingtin expression in clonal striatal cells: dissociation of inclusion formation and neuronal survival by caspase inhibition," *J. Neurosci.*, 19:964–973 (1999).

Klement et al., "Ataxin–1 nuclear localization and aggregation: Role in Polyglutamine–Induced Disease in SCA1 transgenic mice," *Cell*, 95:41–53 (1998).

Koeppen A., "The Purkinje cell and its afferents in human hereditary ataxia," *Neuropathol. Exp. Neurol.*, 50:505–514 (1991).

Koide et al., "Unstable expansion of CAG repeat in hereditary dentatorubral–pallidoluysian atrophy (DRPLA)," *Nature Genet.*, 6:9–13 (1994).

Koyano et al., "Neuronal intranuclear inclusions in spinocerebellar ataxia type 2: triple–labeling immunofluorescent study," *Neurosci. Lett.*, 273: 117–120 (1999).

Kuemmerle et al., "Huntington aggregates may not predict neuronal death in Huntington's disease," *Annals of Neurology*, 46:842–849 (1999).

La Spada et al., "Androgen receptor gene mutations in X–linked spinal and bulbar muscular strophy," *Nature*, 352:77–79 (1991).

Lippa et al., "Lewy bodies contain altered α–synuclein in brains of many familial Alzheimer's disease patients with mutations in presenilin and amyloid precursor genes," *Am. J. Pathol.*, 153:1365–1370 (1998).

Mangiarini et al., "Instability of highly expanded CAG repeats in mice transgenic for the Huntington's disease mutation," *Nature Genet.*, 15:197–200 (1997).

Mangiarini et al., "Exon 1 of the HD gene with an expanded CAG repeat is sufficient to cause a progressive neurological phenotype in transgenic mice," *Cell*, 87:493–506 (1996).

Martindale et al., "Length of huntingtin and its polyglutamine tract influences localization and frequency of intracellular aggregates," *Nature Genet.*, 18:150–154 (1998).

Mezey et al., "Alpha synuclein is present in Lewy bodies in sporadic Parkinson's disease," *Mol. Psychiatry*, 3:493:499 (1998).

Nechiporuk et al., "The mouse *SCA2* gene: cDNA sequence, alternative splicing and protein expression," *Hum. Mol. Genet.*, 7:1301–1309 (1998).

Orr et al., "Expansion of an unstable trinucleotide CAG repeat in spinocerebellar ataxia type 1, "*Nature Genet.*, 4:221–226 (1993).

Paulson H., "Human Genetics '99: Trinucleotide repeats protein fate in neurodegenerative proteinopathies: Polyglutamine Diseases join the (Mis) Fold," *Am. J. Hum. Genet.*, 64:339–345 (1999).

Paulson et al., "Intranuclear inclusions of expanded polyglutamine protien in spinocerebellar ataxia type 3," *Neuron*, 19:333–344 (1997).

Pulst et al., "Moderate expansion of a normally biallelic trinucleotide repeat in spinocerebellar ataxia type 2," *Nature Genet.*, 14:269–276 (1996).

Reddy et al., "Behavioural abnormalities and selective neuronal loss in HD transgenic mice expressing mutated full–length *HD* cDNA," *Nature Genet.*, 20:198–202 (1998).

Sanchez et al., "Caspase–8 is required for cell death induced by expanded polyglutamine repeats," *Neuron*, 22:623–633 (1999).

Sanpei et al., "Identification of the spinocerebellar ataxia type 2 gene using a direct identification of repeat expansion and cloning technique, DIRECT," *Nature Genet.*, 14:277–284 (1996).

Saudou et al., "Huntingtin acts in the nucleus to induce apoptosis but death does not correlate with the formation of intranuclear inclusions," *Cell*, 95:55–66 (1998).

Scherzinger et al., "Huntingtin—encoded polyglutamine expansions form amyloid like protein aggregates in vitro and in vivo," *Cell*, 90:549–558 (1997).

Shibata et al., "A novel protein with RNA–binding motifs interacts with ataxin–2, " *Hum. Mol. Genet.*, 9:1303–1313 (2000).

Stenoien et al., "Polyglutamine—expanded androgen receptors form aggregates that sequester heat shock proteins, proteasome components and SRC–1, and are suppressed by the HDJ–2 chaperone," *Hum. Mol. Genet.*, 8:731–741 (1999).

Trottier et al., "Heterogeneous intracellular localization and expression of ataxin—3," *Neuribiology of Disease*, 5:335–347 (1998).

Vandaele et al., "Purkinje cell protein—2 regulatory regions and transgene expression in cerebellar compartments," *Genes and Develop.*, 5:1136–1148 (1991).

Vig et al., "Reduced immunoreactivity to calcium–binding proteins in Purkinje cells precedes onsets of ataxia in spinocerebellar ataxia–1 transgenic mice," *Neurology*, 50:106–113 (1998).

Wellington et al., "Caspase cleavage of gene products associated with triplet expansion disorders generates truncated fragments containing the polyglutamine tract," *J. Biol. Chem.*, 273:9158–9167 (1998).

Zhuchenko et al., "Autosomal dominant cerebellar ataxia (SCA6) associated with small polyglutamine expansions in the $\alpha_{1A}$–voltage–dependent calcium channel," *Nature Genet.*, 15:62–69 (1997).

Huynh et al., "SCA2: Absence of intranuclear aggregates and animal model," *Neurology* 52(6), suppl. 2:A6 (1999).

Huynh et al., "Nuclear localization or inclusion body formation of ataxin–2 are not necessary for SCA2 pathogenesis in mouse or human," *Nature Genetics* 26:44–50 (2000).

* cited by examiner

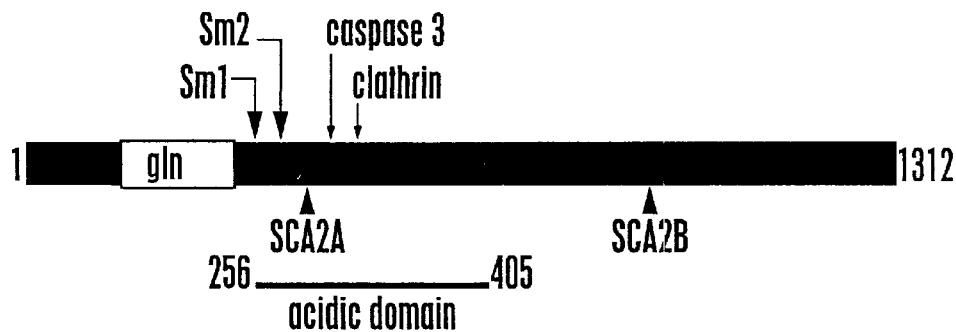
Fig. 1
Fig. 2A
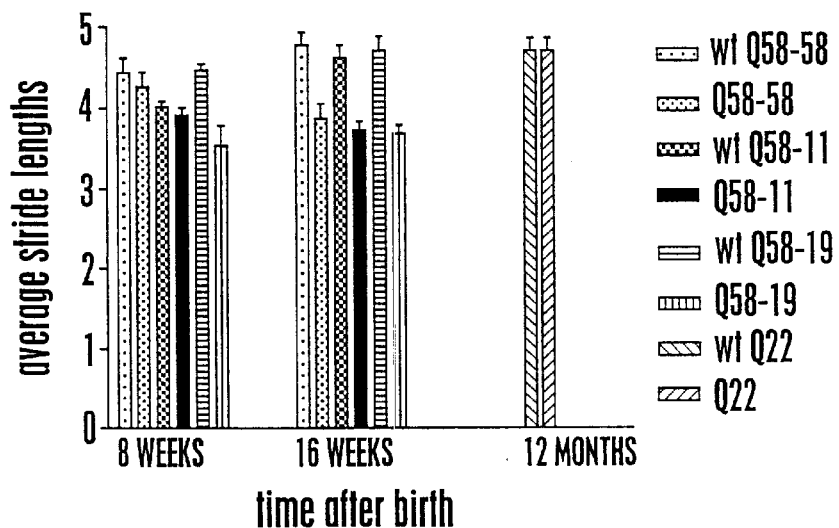
Fig. 2B
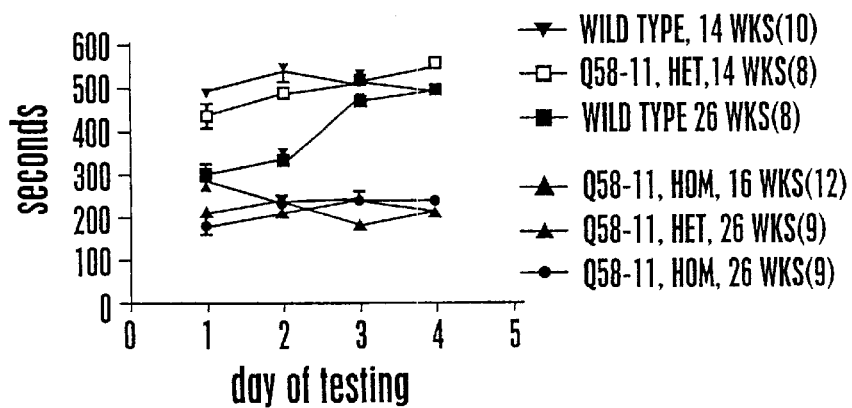

TRANSGENIC MOUSE EXPRESSING A POLYNUCLEOTIDE ENCODING A HUMAN ATAXIN-2 POLYPEPTIDE

This invention was made with government support under grant number NS33123 awarded by the National Institutes of Health. The government has certain rights in the invention.

BACKGROUND OF THE INVENTION

The present invention relates generally to the field of neurobiology and more specifically to a mouse model of neurodegenerative disease.

The hereditary ataxias are a complex group of neurodegenerative disorders characterized by varying abnormalities of balance attributed to dysfunction or pathology of the cerebellum and cerebellar pathways. In many of these disorders, dysfunction or structural abnormalities extend beyond the cerebellum, and can involve basal ganglia function, oculo-motor disorders and neuropathy. The dominant spinocerebellar ataxias (SCAs) represent a heterogeneous group of disorders with a prevalence of familial cases of approximately 1 in 100,000.

A variety of genes and phenotypes have been identified to be associated with a family of neurodegenerative diseases, including SCA1, SCA2, Machado-Joseph disease (SCA3), SCA6, SCA7, Huntington disease, spinal bulbar muscular atrophy, and dentatorubral pallidoluysian atrophy. These diseases are associated with the expansion of a polyglutamine (polyQ) tract in the protein encoded by the respective disease genes.

Although the study of normal and diseased human brains can provide important insights into polyQ-associated disease pathogenesis, such observations are limited to the terminal stages of the disease process. Mouse models can circumvent this problem, but many mouse models of human polyQ diseases rely on the use of truncated constructs or very long polyQ tracts to produce neruodegeneration (Ikeda et al., *Nature Genet.*, 13:196–202 (1996); Mangiarini et al., *Cell*, 87:493–506 (1996); Mangiarini et al., *Nature Genet.*, 15:197–200 (1997); Davies et al., *Phil. Trans. R. Soc. Lond. B Biol. Sci.*, 354:981–989 (1999)). In addition, several polyQ mouse models do not show prominent neuronal loss, a defining feature of human polyQ diseases.

Thus, there exists a need for a non-human animal model of polyQ neurodegenerative disease and methods of identifying therapeutic agents useful for treating neurodegenerative disease. The present invention satisfies this need and provides related advanatages as well.

SUMMARY OF THE INVENTION

The invention provides a transgenic non-human mammal comprising nucleated cells containing a transgene encoding an ataxin-2 polypeptide comprising a polyglutamine tract. In particular, the transgenic non-human mammal can be a mouse. The invention also provides methods of using a transgenic non-human mammal expressing an ataxin-2 polypeptide to identify a therapeutic agent for use in treating a neurodegenerative disease by administering a compound to a transgenic non-human mammal expressing an ataxin-2 polypeptide and screening the transgenic non-human mammal for an improved neurological response associated with a neurodegenerative phenotype of the transgenic non-human mammal, thereby identifying a therapeutic agent for use in treating the neurodegenerative disease.

BRIEF DESCRIPTION OF THE DRAWINGS

FIG. 1 shows a schematic map of ataxin-2. Ataxin-2 is a protein with 1,312 amino acids. Shown are the positions of an acidic domain (amino acids 256–405), two RNA binding motifs, designated Sm1 (amino acids 230–233) and Sm2 (amino acids 283–286), a putative caspase-3 recognition site (amino acids 396–399), and a clathrin-mediated sorting signal (amino acids 414–416), which is downstream of an ER exit signal. The positions of two peptides, SCA2A and SCA2B, against which antibodies were generated, are also indicated.

FIGS. 2(A–B) shows functional loss in transgenic mouse lines expressing human ataxin-2 having 58 polyglutamine repeats. FIG. 2a shows footprinting analysis of wild type and ataxin-2 transgenic mice. FIG. 2b shows rotarod analysis of wild type, homozygous and heterozygous transgenic mice expressing 58 polyglutamines (line Q58–11).

DETAILED DESCRIPTION OF THE INVENTION

The present invention provides a transgenic non-human mammal, in particular a transgenic mouse, comprising nucleated cells containing a transgene encoding an ataxin-2 polypeptide comprising a polyglutamine tract. The transgenic non-human mammal of the invention is useful as a model for neurodegenerative disease. A transgenic non-human mammal expressing a SCA2 gene or the encoded ataxin-2 polypeptide, or cells derived therefrom, can also be advantageously used in methods to identify therapeutic agents useful for treating various neurodegenerative diseases, for example, spinocerebellar ataxia type 1 (SCA1), SCA2, SCA3, SCA4, SCA5, SCA6, SCA7, Huntington disease, spinal bulbar muscular atrophy, Machado-Joseph disease, dentatorubral pallidoluysian atrophy, Alzheimer's disease, Parkinson's disease and amyotrophic lateral sclerosis (ALS; Lou Gehrig's disease).

SCA2 belongs to the growing family of neurodegenerative diseases caused by expansion of a polyglutamine (polyQ) tract. This group now includes SCA1 (Orr et al., *Nature Genet.*, 4:221–226 (1993)); Machado-Joseph disease (SCA3 or MJD) (Kawaguchi et al., *Nature Genet.*, 8:221–228 (1994)); SCA6 (Zhuchenko et al., *Nature Genet.* 15:62–69 (1997)); SCA7 (David et al., *Nature Genet.*, 17:65–70 (1997)); Huntington's disease (HD) (The Huntington's Disease Collaborative Research Group, *Cell*, 72:971–983 (1993)); spinal bulbar muscular atrophy (SBMA) (La Spada et al., *Nature*, 352:77–79 (1991)); and dentatorubral pallidoluysian atrophy (DRPLA) (Koide et al., *Nature Genet.*, 6:9–13 (1994)). Despite their phenotypic differences, evidence has suggested that these diseases share a common pathogenetic mechanism. To some degree, polyQ diseases can be regarded as prototypes of human neurodegenerative diseases caused by mutant and misfolded proteins. Although ubiquitination, intranuclear location of full-length or truncated proteins and caspase cleavage have all been implicated in polyQ pathogenesis, it has been unclear which features are common to polyQ diseases and which features are necessary and sufficient for pathogenesis.

Because intranuclear aggregates are found in a subset of neurons in the brains of patients with SCA3 and Huntington's disease (HD), it has been suggested that formation of intranuclear inclusions (NIs) is a common feature causing polyQ-mediated neuronal death. Intranuclear inclusions were also found in mouse models of human polyQ diseases and in cultured cells when they were transfected with cDNAs containing long CAG repeats (Cummings et al., *Nature Genet.*, 19:148–154 (1998); Paulson et al., *Neuron*, 19:333–344 (1997); Trottier et al., *Neurobiol. Dis.*, 5:335–347 (1998); Holmberg et al., *Hum. Mol. Genet.*, 7:913–918 (1998); Igarashi et al., *Nature Genet.*, 18:111–117 (1998); Davies et al., *Cell*, 90:537–548 (1997); Martindale et al., *Nature Genet.*, 18:150–154 (1998); Saudou et al., *Cell*, 95:55–66 (1998); Scherzinger et al., *Cell*, 90:549–558 (1997); Stenoien et al., *Hum. Mol. Genet.*, 8:731–741 (1999)). Several studies, however, have questioned their importance for pathogenesis. Transgenic mouse lines expressing a truncated amino-terminal huntingtin fragment with more than 130 glutamine repeats had an abundant number of NIs, but there was little evidence for a role for NIs in neurodegeneration (Davies et al., *Cell*, 90:537–548 (1997)). In contrast, mice expressing full-length huntingtin with either 48 or 89 glutamine repeats exhibited striatal neuronal death with few NIs in these neurons (Reddy et al., *Nature Genet.*, 20:198–202 (1998)).

In vitro studies with huntingtin showed that nuclear localization of the mutant protein was required for neurodegeneration (Saudou et al., *Cell*, 95:55–66 (1998)), but the formation of the NIs did not correlate with neuronal death induced by mutant huntingtin (Paulson *Am. J. Hum. Genet.*, 64:339–345 (1999); Gutekunst et al., *J. Neurosci.*, 19:2522–2534 (1999); Kuemmerle et al., *Ann. Neurol.*, 46:842–849 (1999)). In addition, although intranuclear aggregates are found in HD brains, most polyQ aggregation in HD is perinuclear (Gutekunst et al., *J. Neurosci.*, 19:2522–2534 (1999); Kuemmerle et al., *Ann. Neurol.*, 46:842–849 (1999)). On the other hand, for SCA1 pathogenesis, intranuclear location of ataxin-1 was necessary for pathogenesis, although the formation of aggregates was not (Klement et al., *Cell*, 95:41–53 (1998)).

Some NIs show co-localization with ubiquitin, proteasomal proteins or heatshock proteins (Cummings et al., supra, 1998; Paulson et al., supra, 1997; Trottier et al., supra, 1998; Holmberg et al., supra, 1998; Igarashi et al., supra, 1998; Davies et al., supra, 1997; Martindale et al., supra, 1998; Saudou et al., supra, 1998; Scherzinger et al., supra, 1997; Stenoien et al., supra, 1999), suggesting degradation by the ubiquiti-proteasome pathway. The importance of ubiquitination has recently been demonstrated for ataxin-1. Lack of one of the crucial enzymes in ubiquitination, the Ube3 ligase, resulted in decreased inclusions, but increased severity of Purkinje cell pathology in mouse transgenic lines (Cummings et al., *Neuron*, 24:879–892 (1999)). It is unknown whether targeting by the ubiquitin-proteasomal pathway is a common feature of all mutant polyQ proteins, and ataxin-6 did not appear to be ubiquitinated in human SCA6 brains (Ishikawa et al., *Hum. Mol. Genet.*, 8:1185–1193 (1999)).

The protein product of the SCA2 gene, designated ataxin-2, is composed of 1,312 amino acid residues with a calculated molecular weight of 140 kD. The human SCA2 cDNA sequence (SEQ ID NOS:1 and 2 for nucleotide and amino acid sequences, respectively) is available at GenBank accession No. U70323 (Pulst et al., *Nature Genetics* 14:269–276 (1996)). FIG. 1 shows a schematic map of ataxin-2 polypeptide, which can also be referred to as a SCA2 polypeptide. Ataxin-2 has a glutamine reach region (gln) and an acidic domain between amino acids 256 to 405. Within the acidic domain lie two RNA-binding motifs, the Sm1 and Sm2 sites at amino acids 230–233 and amino acids 283–286, respectively, a putative caspase-3 recognition site at amino acids 396–399, and a clathrin-mediated sorting signal at amino acids 414–416 downstream of an endoplasmic reticulum (ER) exit signal. The predicted molecular weight for the caspase-3 cleavage ataxin-2 product is 41.2 kD. The location of two peptides, SCA2A and SCA2B, which were used to generate antibodies, are also shown in FIG. 1.

The most common form of wild-type ataxin-2 contains 22 glutamine repeats flanked by a region of proline- and serine-rich domains. In contrast, mouse ataxin-2 has only one glutamine at the site of the human polyQ tract (Nechiporuk et al., *Hum. Mol. Genet.*, 7:1301–1309 (1998)), suggesting that the normal function of ataxin-2 resides in the regions flanking the CAG repeat. With expansion of the polyQ tract to 34 or more, individuals will develop the SCA2 phenotype. Except for the CAG trinucleotide expansion, the protein product of SCA2 has no similarity with other polyQ proteins (Orr et al., supra, 1993; Kawaguchi et al., supra, 1994; Zhuchenko et al., supra, 1997; David et al., supra, 1997; The Huntington's Disease Collaborative Research Group, supra, 1993; La Spada et al., supra, 1991; Koide et al., supra, 1994; Imbert et al., *Nature Genet.*, 14:285–291 (1996); Pulst et al., *Nature Genet.*, 14:269–276 (1996); Sanpei et al., *Nature Genet.*, 14:277–284 (1996)).

Immunohistochemical studies found that ataxin-2 had a cytoplasmic location in normal brain and was expressed in Purkinje cells and specific groups of brainstem and cortical neurons (Huynh et al., *Ann. Neurol.*, 45:232–241 (1999)). Ubiquitinated intranuclear inclusions have been found only in 1–2% of pontine neurons of SCA2 patients, but not in Purkinje cells, which are the primary target in SCA2 pathology (Koyano et al., *Neurosci. Lett.*, 273:117–120 (1999)).

As disclosed herein, SCA2 pathogenesis does not require intranuclear localization of the protein and mutant ataxin-2 does not form large aggregates or inclusion bodies. Mouse lines expressing mutant ataxin-2 show functional and morphological deficits similar to those of mouse lines expressing mutant ataxin-1 (Burright et al., *Cell*, 82:937–948 (1995); Clark et al., *J. Neurosci.*, 17:7385–7395 (1997); Vandaele et al., *Genes Dev.*, 5:1136–1148 (1991)), but without nuclear localization or a detectable increase in ubiquitin-conjugated protein complexes (see Examples III and IV).

The present invention provides a mutant non-human mammal comprising nucleated cells containing a transgene encoding an ataxin-2 polypeptide comprising a polyglutamine tract. As disclosed herein, a "mutant" refers to a genetic change, for example, a mutant form of a nucleic acid or encoded polypeptide means that the nucleic acid contains a genetic modification relative to a parent nucleic acid such as the wild type form of the nucleic acid. Similary, a "mutant," when used in reference to an animal refers to an animal that has been genetically modified. The genetic modification can be the insertion of a gene, thereby generating a "transgenic" animal. As used herein, a "transgene," when used in reference to a transgenic animal, refers to a gene that is inserted into the germ line of an animal in a manner that ensures its function, replication, and transmission as a normal gene. The genetic modification can also be the deletion or disruption of a gene, thereby generating a "knockout" animal. A "knockout" mutant animal refers to partial or complete suppression of the expression of at least a portion of a protein encoded by an endogenous DNA sequence in a cell. Similarly, a disrupted gene results in complete or partial suppression of expression of the gene.

A mutant animal of the invention can be any non-human mammal such as a mouse. A mutant animal can also be, for example, other non-human mammals such as rat, rabbit, goat, pig, guinea pig, sheep, cow, non-human primate or any non-human mammal. It is understood that mutant animals expressing a SCA2 transgene, in addition to the ataxin-2 mutant mouse disclosed herein, can be used in methods of the invention. In one embodiment of the invention mutant mammal, a human SCA2 gene was introduced into a mouse to generate a transgenic mouse expressing ataxin-2 having a variable length polyglutamine tract (see Example II).

A SCA2 transgenic non-human mammal of the invention contains a SCA2 transgene encoding an ataxin-2 polypeptide comprising a polyglutamine tract. The ataxin-2 polypeptide having a polyglutamine tract can be encoded by a SCA2 gene from any mammal, or a splice variant thereof. For example, a SCA2 nucleic acid or encoded ataxin-2 polypeptide can be a human sequence (GenBank accession No. U70323; SEQ ID NOS:1 and 2), with any of a variable number of glutamines in a polyglutamine tract. Another exemplary mammalian SCA2 nucleic acid and encoded ataxin-2 polypeptide is from mouse (GenBank accession No. U70670; SEQ ID NOS:11 and 12 for nucleotide and amino acid sequences, respectively), with any of a variable number of glutamines in a polyglutamine tract. Any SCA2 nucleic acid or encoded ataxin-2 polypeptide from a mammalian species can be used in the invention, with a naturally occurring polyglutamine tract or a polyglutamine tract artificially inserted into the appropriate position in an ataxin-2 polypeptide, for example, to result in a neurodegenerative phenotype. Other exemplary mammalian species include rat, rabbit, goat, pig, guinea pig, sheep, cow, dog, cat, non-human primate, and the like, or any non-human mammal.

For example, it is envisioned that a polyglutamine tract can be inserted into the position of the single glutamine in mouse SCA2 cDNA to generate an ataxin-2 polypeptide having a polyglutamine tract that results in a neurodegenerative phenotype. Similarly, any mammalian SCA2 cDNA can be modified to encode an ataxin-2 polypeptide having at least a minimum number of polyglutamines to result in a neurodegenerative phenotype.

An ataxin-2 polypeptide can be, for example, the human amino acid sequence referenced as SEQ ID NO:2, the mouse amino acid sequence referenced as SEQ ID NO:12, or an ataxin-2 polypeptide from any mammalian species, with the addition or deletion of glutamines to provide a polyglutamine tract to generate an ataxin-2 polypeptide referenced below having between 1 and about 250 glutamines in a polyglutamine tract. As used herein, the term "polypeptide" is intended to refer to a peptide or polypeptide of two or more amino acids. The term "polypeptide analog" includes any polypeptide having an amino acid sequence substantially the same as a sequence specifically described herein in which one or more residues have been conservatively substituted with a functionally similar residue and which displays the ability to functionally mimic an ataxin-2 polypeptide, as described herein. A "modification" of an ataxin-2 polypeptide also encompasses conservative substitutions of an ataxin-2 polypeptide amino acid sequence. Conservative substitutions of encoded amino acids include, for example, amino acids that belong within the following groups: (1) non-polar amino acids (Gly, Ala, Val, Leu, and Ile); (2) polar neutral amino acids (Cys, Met, Ser, Thr, Asn, and Gln); (3) polar acidic amino acids (Asp and Glu); (4) polar basic amino acids (Lys, Arg and His); and (5) aromatic amino acids (Phe, Trp, Tyr, and His). Other minor modifications are included within ataxin-2 polypeptides so long as the polypeptide retains some or all of the structural and/or functional characteristics of an ataxin-2 polypeptide. Exemplary structural characteristics include sequence identity or substantial similarity, antibody reactivity, and presence of conserved structural domains such as RNA binding domains or acidic domains.

As with an ataxin-2 polypeptide, the invention also provides a functional derivative of an ataxin-2 polypeptide. The term "functional", when used herein as a modifier of an invention ataxin-2 polypeptide, or polypeptide fragment thereof, refers to a polypeptide that exhibits functional characteristics similar to ataxin-2 polypeptide. Exemplary functional characteristics of ataxin-2 polypeptide include RNA binding, transport of molecules, or exhibiting a potential neurodegenerative phenotype based on the size of the polyglutamine tract, that is, an ataxin-2 polypeptide having fewer polyglutamines has a normal phenotype and an ataxin-2 polypeptide having a greater number of polyglutamines has a neurodegenerative phenotype, for example, 32 or greater polyglutamines. One skilled in the art can readily determine whether a polypeptide, or encoding nucleic acid sequence, is substantially the same as a reference sequence by comparing functional characteristics of the encoded polypeptides to a reference ataxin-2 polypeptide.

Exemplary ataxin-2 polypeptides useful for the production of invention transgenic animals contain polyglutamine (polyQ) tracts of various lengths. For example, the invention provides transgenic mice expressing human ataxin-2 polypeptide having 22 or 58 polyglutamines (see Example II). The invention also provides non-human mammals and corresponding DNA constructs expressing SCA2 cDNA encoding ataxin-2 polypeptides having from 1 to greater than 250 polyglutamines and in particular about 22 to about 58 polyglutamines. The polyglutamine tract can be contiguous, or can contain short segments of non-glutamine amino acids. The length of the polyglutamine tract determines whether an animal or cell exhibits a neurodegenerative phenotype.

Depending on the genetic background and stochastic changes, an ataxin-2 polypeptide having about 32 polyglutamines or greater generally result in a neurodegenerative phenotype. Accordingly, the invention provides transgenic non-human mammals and cells expressing a SCA2 transgene encoding an ataxin-2 polypeptide having about 32 or more, about 35 or more, about 40 or more, about 45 or more, about 50 or more, about 55 or more, about 60 or more, about 65 or more, about 70 or more, about 75 or more, about 80 or more, about 95 or more, about 100 or more, about 120 or more, about 150 or more, about 175 or more, about 200 or more, or even about 250 or more glutamines in a polyglutamine tract and exhibiting a neurodegenerative phenotype. Animals or cells expressing such a SCA2 transgene are particularly useful as a model of neurodegenerative disease and can be used in methods of the invention to identify therapeutic agents for use in treating a neurodegenerative disease, as disclosed herein.

Generally, polyglutamine tracts of up to about 30 repeats are normal, that is, do not display a neurodegenerative phenotype. The invention provides a transgenic non-human mammal expressing a SCA2 encoding an ataxin-2 polypeptide having between 1 and about 30 polyglutamines, for example, about 5 to about 30, about 10 to about 25, and in particular about 22 polyglutamines (see Example III). Accordingly, the ataxin-2 polypeptide can contain about 1, about 5, about 10, about 15, about 20, about 22, about 25, about 28, or about 30 polyglutamines, or higher numbers so long as the ataxin-2 polypeptide does not result in a neurodegenerative phenotype. Such animals, or cells expressing corresponding transgenes, are particularly useful as controls for an animal or cell exhibiting a neurodegenerative phenotype.

In a particular embodiment, the invention provides a homozygous SCA2 mutant non-human mammal, in which two alleles of the SCA2 transgene are present. In another embodiment, the invention further provides a heterozygous SCA2 mutant non-human mammal, in which only one allele of the SCA2 transgene is present.

The invention SCA2 mutant non-human mammals can be produced by creating transgenic animals expressing a SCA2 cDNA encoding an ataxin-2 polypeptide using a variety of techniques. Examples of such techniques include the insertion of normal or mutant versions of nucleic acids encoding an ataxin-2 polypeptide by microinjection, retroviral infection or other means well known to those skilled in the art, into appropriate fertilized embryos to produce a transgenic animal (Hogan et al., *Manipulating the Mouse Embryo: A Laboratory Manual*, Cold Spring Harbor Laboratory (1986), and U.S. Pat. Nos. 5,616,491 and 5,750,826), as described below in more detail.

Mouse models of human polyQ diseases have been very instructive in elucidating the morphological and biochemical steps important for pathogenesis. Several unresolved questions involve the subcellular localization of polyQ proteins, their need for aggregation and the importance of truncation in pathogenesis. The SCA2 transgenic mouse lines disclosed herein share important features with ataxin-1 lines, including the promoter driving the expression of the transgene, the use of full-length cDNAs, and the time course and nature of pathological and functional changes. Despite these similarities, the localization of the respective proteins are very different. Thus, the SCA2 mutant mouse of the invention is useful for elucidating the mechanism for development of polyQ diseases as well as methods for treating polyQ diseases.

Several mutant proteins that are involved in polyQ diseases form intranuclear inclusions (Cummings et al., supra, 1998; Paulson et al., supra, 1997; Trottier et al., supra, 1998; Holmberg et al., supra, 1998; Igarashi et al., supra, 1998; Davies et al., supra, 1997; Martindale et al., supra, 1998; Saudou et al., supra, 1998; Scherzinger et al., supra, 1997; Stenoien et al., supra, 1999; Paulson, supra, 1999), leading to the hypothesis that intranuclear aggregation of mutant polyQ proteins was a common pathological mechanism for polyQ diseases. This appeared to be correct for both proteins that contain nuclear localization signals (such as ataxin-1) and proteins that lack these signals (such as ataxin-3, which is a cytoplasmic and nuclear protein) (Trottier et al., *Neurobiol. Dis.*, 5:335–347 (1998); Paulson et al., *Neuron*, 19:333–344 (1997)). Ataxin-2 appears to belong to the latter group, in that the protein does not contain any of the known nuclear localization signals and has an exclusively cytoplasmic localization in normal and SCA2 human brain (Huynh et al., *Ann. Neurol.*, 45:232–241 (1999)).

Evidence from a YAC transgenic model of HD suggested that only truncated N-terminal huntingtin enters the nucleus (Hodgson et al., *Neuron*, 23:181–192 (1999)). Despite this fact, there was little correlation of behavioural deficits with the presence of nuclear N-terminal huntingtin aggregates, suggesting that large nuclear aggregates are unlikely to be causal in Huntington disease neurodegeneration, although they possibly important for disease progression (Hodgson et al., supra, 1999).

As disclosed herein, intranuclear localization is not necessary for all classes of polyQ pathogenesis or for disease progression, in particular, SCA2. The finding that cytoplasmic localization and microaggregation or accumulation of ataxin-2 cause Purkinje cell pathogenesis places SCA2 into the larger group of neurodegenerative diseases where protein aggregation occurs in the cytoplasm, for example, Parkinson disease, Alzheimer disease, and SCA6 (Mezey et al., *Mol. Psychiatry*, 3:493–499 (1998); Lippa et al., *Am. J. Pathol.*, 153:1365–1370 (1998); Ishikawa et al., *Hum. Mol. Genet.*, 8:1185–1193 (1999)). Therefore, the SCA2(58) transgenic mouse is useful as an animal model for other neurodegenerative diseases, including studies to characterize similarities and differences in neurodegenerative diseases involving cytoplasmic versus nuclear aggregation mechanisms as well as methods of treatment, as described below.

A transgenic non-human mammal of the invention can exhibit a neurodegenerative phenotype and is useful as an animal model of neurodegenerative disease. As used herein, a "neurodegenerative phenotype" refers to a functional or morphological change associated with a neurodegenerative disease. A functional change associated with a neurodegenerative phenotype includes any of a variety of behavioral changes associated with neurodegenaration. Such behavioral changes can include, for example in a mouse model, clasping, stride length, motor coordination and balance (see Example III). Other exemplary behavioral changes include memory changes, which can be tested using a Morris water maze or other methods of testing memory.

A morphological change associated with a neurodegenerative phenotype includes any of a variety of structural, anatomic or histological changes. Such morphological changes can include changes in protein expression in particular cell types, changes in the number or size of particular cells or particular cell structures. For example, as disclosed herein, a neurodegenerative phenotype associated with SCA2 expression includes changes in calbindin-28K expression, which is specifically expressed in cytoplasm and dendritic processes of cerebellar Purkinje cells (see Example IV). Other morphological changes include loss of dendritic arbour, a decrease in Purkinje cell numbers, and formation of inclusion bodies. Other exemplary morphological changes include changes in neurotransmitter or enzyme concentrations or changes in expression of proteins associated with neurodegenerative disease such as proteins regulating calcium homeostasis, protein folding, or ubiquitination, in particular, changes in proteins expressed in neuronal cells.

A DNA fragment encoding an ataxin-2 polypeptide can be integrated into the genome of the transgenic animal by any standard method well known to those skilled in the art. Any of a variety of techniques known in the art can be used to introduce the transgene into animals to produce the founder lines of transgenic animals (see, for example, Hogan et al., *Manipulating the Mouse Embryo: A Laboratory Manual* Cold Spring Harbor Laboratory (1986); Hogan et al., *Manipulating the Mouse Embryo: A Laboratory Manual*, second ed., Cold Spring Harbor Laboratory (1994), U.S. Pat. Nos. 5,602,299; 5,175,384; 6,066,778; and 6,037,521). Such techniques include, but are not limited to, pronuclear microinjection (U.S. Pat. No. 4,873,191); retrovirus mediated gene transfer into germ lines (Van der Putten et al., *Proc. Natl. Acad. Sci. USA* 82:6148–6152 (1985)); gene targeting in embryonic stem cells (Thompson et al., *Cell* 56:313–321 (1989)); electroporation of embryos (Lo, *Mol Cell. Biol.* 3:1803–1814 (1983)); and sperm-mediated gene transfer (Lavitrano et al., *Cell* 57:717–723 (1989)).

For example, embryonal cells at various developmental stages can be used to introduce transgenes for the production of transgenic animals. Different methods are used depending on the stage of development of the embryonal cell. The zygote is a good target for micro-injection, and methods of microinjecting zygotes are well known to (see U.S. Pat. No. 4,873,191). In the mouse, the male pronucleus reaches the size of approximately 20 micrometers in diameter which allows reproducible injection of 1–2 picoliters (pl) of DNA solution. The use of zygotes as a target for gene transfer has a major advantage in that in most cases the injected DNA will be incorporated into the host genome before the first cleavage (Brinster, et al. *Proc. Natl. Acad. Sci. USA*

82:4438–4442 (1985)). As a consequence, all cells of the transgenic non-human animal will carry the incorporated transgene. This will in general also be reflected in the efficient transmission of the transgene to offspring of the founder since 50% of the germ cells will harbor the transgene. Micro-injection of SCA2 nucleic acid fragments were microinjected into pronuclei to generate SCA2 transgenic mouse (see Example II).

The transgenic animals of the present invention can also be generated by introduction of the targeting vectors into embryonal stem (ES) cells. ES cells are obtained by culturing pre-implantation embryos in vitro under appropriate conditions (Evans et al., *Nature* 292:154–156 (1981); Bradley et al., *Nature* 309:255–258 (1984); Gossler et al., *Proc. Natl. Acad. Sci. USA* 83:9065–9069 (1986); and Robertson et al., *Nature* 322:445–448 (1986)). Transgenes can be efficiently introduced into the ES cells by DNA transfection using a variety of methods known to the art including electroporation, calcium phosphate co-precipitation, protoplast or spheroplast fusion, lipofection and DEAE-dextran-mediated transfection. Transgenes can also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (reviewed in Jaenisch, *Science* 240:1468–1474 (1988)). Prior to the introduction of transfected ES cells into the blastocoel, the transfected ES cells can be subjected to various selection protocols to enrich for ES cells that have integrated the transgene if the transgene provides a means for such selection. Alternatively, PCR can be used to screen for ES cells that have integrated the transgene. This technique obviates the need for growth of the transfected ES cells under appropriate selective conditions prior to transfer into the blastocoel.

In addition, retroviral infection can also be used to introduce transgenes into a non-human animal. The developing non-human embryo can be cultured in vitro to the blastocyst stage. During this time, the blastomeres can be targets for retroviral infection (Janenich *Proc. Natl. Acad. Sci. USA* 73:1260–1264 (1976)). Efficient infection of the blastomeres is obtained by enzymatic treatment to remove the zona pellucida (Hogan et al., supra, 1986). The viral vector system used to introduce the transgene is typically a replication-defective retrovirus carrying the transgene (Jahner et al., *Proc. Natl. Acad Sci. USA* 82:6927–6931 (1985); Van der Putten, et al. *Proc. Natl. Acad Sci. USA* 82:6148–6152 (1985)). Transfection is easily and efficiently obtained by culturing the blastomeres on a monolayer of virus-producing cells (Van der Putten, supra, 1985; Stewart et al., *EMBO J.* 6:383–388 (1987)). Alternatively, infection can be performed at a later stage. Virus or virus-producing cells can be injected into the blastocoele (Jahner D. et al., *Nature* 298:623–628 (1982)). Most of the founders will be mosaic for the transgene since incorporation occurs only in a subset of cells which form the transgenic animal. Further, the founder can contain various retroviral insertions of the transgene at different positions in the genome, which generally will segregate in the offspring. In addition, it is also possible to introduce transgenes into the germline by intrauterine retroviral infection of the midgestation embryo (Jahner et al., supra, 1982). Additional means of using retroviruses or retroviral vectors to create transgenic animals known to the art involves the micro-injection of retroviral particles or mitomycin C-treated cells producing retrovirus into the perivitelline space of fertilized eggs or early embryos (WO 90/08832 (1990); Haskell and Bowen *Mol. Reprod. Dev.* 40:386 (1995)).

A DNA fragment comprising a SCA2 cDNA encoding an ataxin-2 polypeptide can be microinjected into pronuclei of single-cell embryos in non-human mammals such as a mouse (see Example II). The injected embryos are transplanted to the oviducts/uteri of pseudopregnant females and finally transgenic animals are obtained.

Once the founder animals are produced, they can be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic mice to produce mice homozygous for a given integration site in order to both augment expression and eliminate the need for screening of animals by DNA analysis; crossing of separate homozygous lines to produce compound heterozygous or homozygous lines; breeding animals to different inbred genetic backgrounds so as to examine effects of modifying alleles on expression of the transgene and the neuropathological effects of expression.

The present invention provides transgenic non-human mammals that carry the transgene in all their cells, as well as animals that carry the transgene in some, but not all their cells, that is, mosaic animals. The transgene can be integrated as a single transgene or in concatamers, for example, head-to-head tandems or head-to-tail tandems.

The transgenic animals are screened and evaluated to select those animals having a neurodegenerative phenotype, which are animal models for neurodegenerative disease. Initial screening can be performed using, for example, Southern blot analysis or PCR techniques to analyze animal tissues to verify that integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and reverse transcriptase-PCR (rt-PCR). Samples of brain or other suitable tissues can be evaluated immunocytochemically using antibodies specific for an ataxin-2 polypeptide or a tag such as GFP (see Example IV). The transgenic non-human mammals can be further characterized to identify those animals having a neurodegeneratve phenotype useful in methods of the invention. In particular, transgenic non-human mammals expressing ataxin-2 polypeptides having variable numbers of glutamines in a polyglutamine tract can be screened for a neurodegenerative phenotype using the methods disclosed herein.

The invention also provides a mutant animal having a disrupted SCA2 gene, that is, a knockout animal. Methods for generating a mutant animal having a disrupted SCA2 gene are well known to those skilled in the art as described, for example, in Shastry, *Experentia* 51:1028–1039 (1995); Shastry, *Mol. Cell. Biochem.* 181:163–179 (1998); and U.S. Pat. No. 5,616,491, issued Apr. 1, 1997, No. 5,750,826, issued May 12, 1998, and No.5,981,830, issued Nov. 9, 1999. For example, a mutant animal can be generated by introducing into an embryonic stem cell a DNA construct having an appropriate insertion in a gene such that homologous recombination of the introduced gene in the embryonic stem cell results in disruption of the gene. A knockout animal can further be modified, if desired, to express a heterologous SCA2 transgene, as disclosed herein.

The invention additionally provides cells isolated from an invention transgenic non-human mammal. For example, the invention provides isolated mouse cells derived from an invention SCA2 transgenic mouse. Cells derived from an invention transgenic.non-human mammal can be used, for example, in methods of identifying a therapeutic agent for treating neurodegenerative disease, as described in more detail below.

The invention additionally provides a DNA construct comprising a nucleic acid encoding an ataxin-2 polypeptide having a polyglutamine tract, preferably a mammalian ataxin-2 and in particular a human ataxin-2. The term "nucleic acid", also referred to as polynucleotides, encompasses ribonucleic acid (RNA) or deoxyribonucleic acid (DNA), probes, oligonucleotides, and primers and can be single stranded or double stranded. DNA can be either complementary DNA (cDNA) or genomic DNA, and can represent the sense strand, the anti-sense strand or both. Examples of nucleic acids are RNA, cDNA, or isolated genomic DNA encoding an ataxin-2 polypeptide. When expressed in a transgenic animal, the DNA construct comprises a transgene.

The DNA construct contains a poly CAG or poly CAA that encodes the polyglutamine tract. The DNA construct can comprise the nucleotide sequence of human SCA2 cDNA referenced as SEQ ID NO:1 (GenBank accession No. U70323), with the addition or deletion of glutamines to provide a polyglutamine tract to generate an ataxin-2 polypeptide referenced above having between 1 and about 250 glutamines in the polyglutamine tract. The DNA construct can also comprise the nucleotide sequence of mouse SCA2 cDNA reference as SEQ ID NO:11 (GenBank accession No. U70670), or SCA2 cDNAS from other mammalian species, any of which can similarly be modified to contain between 1 and 250 glutamines in a polyglutamine tract. Thus, the polyglutamine tract can contain a naturally occurring number of glutamines or can be modified to contain 1 to about 250, or more, glutamines in a polyglutamine tract. The nucleic acid encoding ataxin-2 polypeptide can be the same or substantially the same as a reference SCA2 nucleic acid sequence, so long as the encoded ataxin-2 polypeptide exhibits structural and/or functional characteristics of an ataxin-2 polypeptide. Exemplary structural characteristics include sequence identity or substantial similarity, antibody reactivity, and presence of conserved structural domains such as RNA binding domains or acidic domains. Exemplary functional characteristics of an ataxin-2 polypeptide include RNA binding, transport of molecules, and/or exhibiting a potential neurodegenerative phenotype based on the size of the polyglutamine tract, that is, an ataxin-2 having fewer polyglutamines has a normal phenotype and an ataxin-2 having a greater number of polyglutamines has a neurodegenerative phenotype, for example, 32 or greater polyglutamines. One skilled in the art can readily determine whether a nucleic acid sequence is substantially the same as a reference sequence by comparing functional characteristics of the encoded polypeptides to a reference ataxin-2 polypeptide.

As employed herein, the term "substantially the same nucleotide sequence" refers to DNA having sufficient identity to the reference polynucleotide, such that it will hybridize to the reference nucleotide under moderately stringent, or higher stringency, hybridization conditions. DNA having "substantially the same nucleotide sequence" as the reference nucleotide sequence can have at least 60%, at least 70%, at least 80%, at least 90%, or at least 95% identity with respect to the reference nucleotide sequence.

A SCA2 nucleic acid can also include a modification of SCA2 cDNA. As used herein, a "modification" of a nucleic acid can also include one or several nucleotide additions, deletions, or substitutions with respect to a reference sequence. A modification of a nucleic acid can include substitutions that do not change the encoded amino acid sequence due to the degeneracy of the genetic code. Such modifications can correspond to variations that are made deliberately, or which occur as mutations during nucleic acid replication.

Exemplary modifications of the SCA2 sequences include sequences that correspond to homologs of other species, including mammalian species such as mouse, primates, including monkey and baboon, rat, rabbit, bovine, porcine, ovine, canine, feline, or other animal species. The corresponding SCA2 sequences of non-human species can be determined by methods known in the art, such as by PCR or by screening genomic, cDNA or expression libraries.

The phrase "moderately stringent hybridization" refers to conditions that permit target-nucleic acid to bind a complementary nucleic acid. The hybridized nucleic acids will generally have at least about 60% identity, at least about 75% identity, more at least about 85% identity; at least about 90% identity; or at least about 95% identity. Moderately stringent conditions are conditions equivalent to hybridization in 50% formamide, 5×Denhart's solution, 5×SSPE, 0.2% SDS at 42° C., followed by washing in 0.2×SSPE, 0.2% SDS, at 42° C.

High stringency hybridization refers to conditions that permit hybridization of only those nucleic acid sequences that form stable hybrids in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5×Denhart's solution, 5×SPE, 0.2% SDS at 42° C., followed by washing in 0.1×SSPE, and 0.1% SDS at 65° C.

Low stringency hybridization refers to conditions equivalent to hybridization in 10% formamide, 5×Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable moderate stringency and high stringency hybridization buffers and conditions are well known to those of skill in the art and are described, for example, in Sambrook et al., *Molecular Cloning: A Laboratory Manual*, 2nd ed., Cold Spring Harbor Press, Plainview, N.Y. (1989); Ausubel et al. (*Current Protocols in Molecular Biology* (Supplement 47), John Wiley & Sons, New York (1999)).

The invention provides a DNA construct comprising nucleic acid encoding an ataxin-2 polypeptide. As used herein, the term "DNA construct" refers to a specific arrangement of genetic elements in a DNA molecule. In addition to human SCA2, or mutant forms thereof encoding a variable number of glutamines in a polyglutamine tract, the invention also provides SCA2 from other species as well as SCA2 mutant non-human mammals expressing SCA2 from non-human species. For example, the invention provides a DNA construct comprising nucleic acid encoding an ataxin-2 polypeptide operationally linked to a Purkinje cell-specific expression element. The invention additionally provides SCA2-green fluorescent protein (GFP) construct (see Example I).

DNA constructs of the invention can be incorporated into vectors for propagation or transfection into appropriate cells to generate invention SCA2 mutant non-human mammals. One skilled in the art can select a vector based on desired properties, for example, for production of a vector in a particular cell such as a mammalian cell or a bacterial cell. If desired, the DNA constructs can be engineered to be operably linked to appropriate expression elements such as promoters or enhancers to allow expression of a genetic element in the DNA construct in an appropriate cell or tissue, for example, a Purkinje cell-specific promoter (see Example II).

The invention also provides vectors containing a SCA2 encoding an ataxin-2 polypeptide having a polyglutamine tract. Suitable expression vectors are well-known in the art and include vectors capable of expressing nucleic acid operatively linked to a regulatory sequence or element such as a promoter region or enhancer region that is capable of regulating expression of such nucleic acid. Appropriate expression vectors include those that are replicable in eukaryotic cells and/or prokaryotic cells and those that remain episomal or those which integrate into the host cell genome.

Regulatory elements, including promoters or enhancers can be constitutive or regulated, depending upon the nature of the regulation, and can be expressed in a variety of tissues, or one or a few specific tissues. The regulatory sequences or regulatory elements are operatively linked to a nucleic acid of the invention such that the physical and functional relationship between the nucleic acid and the regulatory sequence allows transcription of the nucleic acid. Vectors useful for expression in eukaryotic cells can include, for example, regulatory elements including the SV40 early promoter, the cytomegalovirus (CMV) promoter, the mouse mammary tumor virus (MMTV) steroid-inducible promoter, Moloney murine leukemia virus (MMLV) promoter, and the like.

Vectors can contain a regulatory element that provides tissue specific or inducible expression of an operatively linked nucleic acid. One skilled in the art can readily determine an appropriate tissue-specific promotor or enhancer that allows expression of an ataxin-2 polypeptide or nucleic acid in a desired tissue. For example, SCA2 can be operatively linked to a Purkinje cell-specific regulatory element, as disclosed herein (see Example II). Such a vector having a Purkinje cell-specific regulatory element allows expression of SCA2 primarily in Purkinje cells.

Any of a variety of inducible promoters or enhancers can also be included in the vector for regulatable expression of a ataxin-2 polypeptide or nucleic acid. Such inducible systems, include, for example, tetracycline inducible system (Gossen & Bizard, *Proc. Natl. Acad. Sci. USA*, 89:5547–5551 (1992); Gossen et al., *Science*, 268:1766–1769 (1995); Clontech, Palo Alto, Calif.); metalothionein promoter induced by heavy metals; insect steroid hormone responsive to ecdysone or related steroids such as muristerone (No et al., *Proc. Natl. Acad. Sci. USA*, 93:3346–3351 (1996); Yao et al., *Nature*, 366:476–479 (1993); Invitrogen, Carlsbad, Calif.); mouse mammory tumor virus (MMTV) induced by steroids such as glucocortocoid and estrogen (Lee et al., Nature, 294:228–232 (1981); and heat shock promoters inducible by temperature changes.

If desired, the vector can contain a selectable marker. As used herein, a "selectable marker" refers to a genetic element that provides a selectable phenotype to a cell in which the selectable marker has been introduced. A selectable marker is generally a gene whose gene product provides resistance to an agent that inhibits cell growth or kills a cell. A variety of selectable markers can be used in the DNA constructs of the invention, including, for example, Neo, Hyg, hisD, Gpt and Ble genes, as described, for example in Ausubel et al. (*Current Protocols in Molecular Biology* (Supplement 47), John Wiley & Sons, New York (1999)) and U.S. Pat. No. 5,981,830. Drugs useful for selecting for the presence of a selectable marker includes, for example, G418 for Neo, hygromycin for Hyg, histidinol for hisD, xanthine for Gpt, and bleomycin for Ble (see Ausubel et al., supra, (1999); U.S. Pat. No. 5,981,830). DNA constructs of the invention can incorporate a positive selectable marker, a negative selectable marker, or both (see, for example, U.S. Pat. No. 5,981,830).

When a DNA construct is used to disrupt the expression of an endogenous gene in an animal by homologous recombination, the homologous sequence can be chosen from any genomic sequence so long as recombination of the endogenous gene with the homologous region in the DNA construct leads to disruption of the endogenous gene. In particular, the homologous sequence can contain an exon. The DNA construct is inserted into a cell and integrates with the genomic DNA of the cell in such a position so as to prevent or interrupt transcription of the native DNA sequence. When used to disrupt the expression of an endogenous gene in an animal, the DNA construct will generally contain an insert in the homologous region.

The invention additionally provides a cell comprising a DNA construct of the invention. For example, the cell can be an embryonic stem cell. As used herein, an "embryonic stem cell" is pluripotent stem cell derived from an embryo of a cognate organism for which introduction of a transgene is desired. In particular, the invention provides an embryonic stem cell comprising a DNA construct comprising a nucleic acid encoding an ataxin-2 polypeptide. Methods of using embryonic stem cells to generate a SCA2 mutant non-human mammal are well known to those skilled in the art, as disclosed herein. For generation of a mutant mouse, embryonic stem cells can be obtained from a mouse. Alternatively, an appropriate embryonic stem cell line can be used to introduce a DNA construct of the invention.

The invention further provides an isolated cell containing a DNA construct of the invention (see Example I). The DNA construct can be introduced into a cell by any of the well known transfection methods (Sambrook et al., *Molecular Cloning: A Laboratory Manual*, 2nd ed., Cold Spring Harbor Press, Plainview, N.Y. (1989); Ausubel et al., supra, (1999)). Alternatively, the cell can be obtained by isolating a cell from a mutant non-human mammal of the invention and establishing primary cultures. Thus, the invention provides a cell isolated from a SCA2 mutant non-human mammal of the invention, in particular, a SCA2 mutant mouse. The cells can be obtained from a homozygous SCA2 mutant mouse or a heterozygous SCA2 mutant non-human mammal such as a mouse.

The SCA2 mutant non-human mammal of the invention is particularly useful as a model for neurodegenerative disease, particularly for neurodegenerative disease having a common pathogenic mechanism as SCA2, that is, formation of inclusion bodies. Exemplary neurodegenerative disorders include spinocerebellar ataxia type 1 (SCA1), SCA2, SCA3, SCA4, SCA5, SCA6, SCA7, Huntington disease, spinal bulbar muscular atrophy, Machado-Joseph disease, and dentatorubral pallidoluysian atrophy. The invention SCA2 mutant non-human mammal is also useful as a model for Parkinson's disease, Alzheimer's disease, and amyotrophic lateral sclerosis (ALS), which share a similar pathogenic mechanism of the misfolding of proteins, formation of protein aggregates, or formation of inclusion bodies. As a model of various neurodegenerative diseases, the invention SCA2 mutant non-human mammal is useful for identifying a therapeutic agent for treatment of neurodegenerative disease.

The SCA2 mutant non-human mammal of the invention can be advantageously used to screen for therapeutic agents that can be used to treat a neurodegenerative disease. The invention thus provides a method of identifying a therapeutic agent for use in treating a neurodegenerative disease by administering a compound to a SCA2 mutant non-human mammal and screening the mutant non-human mammal for an improved neurological response associated with a neurodegenerative phenotype of the transgenic non-human mammal, thereby identifying a therapeutic agent for use in treating the neurodegenerative disease.

As used herein, "improved neurological response" refers to any change in neurodegenerative phenotype that is expected to result in a less severe neurodegenerative phenotype. Such changes include improved functional and morphological changes associated with a neurodegenerative phenotype. Improved functional changes include behavior more similar to a control, for example, clasping, stride length, motor coordination and balance, memory, and the like. Improved morphological changes include polypeptide expression more similar to a control, or a larger number of Purkinje cells or a decrease in inclusion bodies relative to a transgenic animal exhibiting a neurodegenerative phenotype,.

If desired, appropriate control animals can be used to corroborate the therapeutic effectiveness of screened compounds. For example, a control animal can be one that is not expressing SCA2 or not expressing a SCA2 transgene. Alternatively, a control animal can express a form of an ataxin-2 polypeptide that does not result in a neurodegenerative phenotype, for example, those forms of ataxin-2 polypeptide having fewer than a minimal number of glutamines in a polyglutamine tract sufficient for producing a neurodegenerative phenotype. For example, SCA2(22) can function as a control for SCA2(58) (see Example III).

Compounds useful as potential therapeutic agents can be generated by methods well known to those skilled in the art, for example, well known methods for producing pluralities of compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422–428 (1998); Tietze et al., *Curr. Biol.*, 2:363–371 (1998); Sofia, *Mol. Divers.* 3:75–94 (1998); Eichler et al., *Med. Res. Rev.* 15:481–496 (1995); and the like. Libraries containing large numbers of natural and synthetic compounds also can be obtained from commercial sources. Combinatorial libraries of molecules can be prepared using well known combinatorial chemistry methods (Gordon et al., *J. Med. Chem.* 37: 1233–1251 (1994); Gordon et al., *J. Med. Chem.* 37: 1385–1401 (1994); Gordon et al., *Acc. Chem. Res.* 29:144–154 (1996); Wilson and Czarnik, eds., *Combinatorial Chemistry: Synthesis and Application*, John Wiley & Sons, New York (1997)).

Compounds identified as therapeutic agents by methods of the invention can be administered to an individual, for example, to alleviate a sign or symptom associated a neurodegenerative disease. One skilled in the art will know or can readily determine the alleviation of a sign or symptom associated with a neurodegenerative disease. Such symptoms of a neurodegenerative disease include weakness, spasticity, movement disorders, memory loss, dementia, and the like.

For use as a therapeutic agent, the compound can be formulated with a pharmaceutically acceptable carrier to produce a pharmaceutical composition, which can be administered to the individual, which can be a human or other mammal. A pharmaceutically acceptable carrier can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester. A pharmaceutically acceptable carrier can also contain physiologically acceptable compounds that act, for example, to stabilize or increase the absorption of the modulatory compound. One skilled in the art would know that the choice of a pharmaceutically acceptable carrier, including a physiologically acceptable compound, depends, for example, on the route of administration of the composition.

The methods of the invention can advantageously use cells isolated from a homozygous or heterozygous SCA2 mutant non-human mammal, for example, nerve cells, fibroblasts, muscle cells, or any appropriate cell isolated from a SCA2 mutant non-human of the invention for a desired purpose. The methods of the invention can also be used with cells expressing SCA2 encoding an ataxin-2 polypeptide such as a transfected cell line (see Example I).

A cell expressing a SCA2 encoding an ataxin-2 polypeptide can be used as an in vitro method to screen compounds as potential therapeutic agents for treating neurodegenerative disease. In such a method, a compound is contacted with a cell expressing SCA2, either a transfected cell or a cell derived from a SCA2 mutant non-human mammal, and screened for alterations in a phenotype associated with expression of SCA2. For example, cells expressing a SCA2 mutant that forms inclusion bodies, such as SCA2(58), can be used to screen for compounds that inhibit or prevent formation of the inclusion bodies.

An ataxin-2 fusion polypeptide such as ataxin-2-GFP can be particularly useful for such screening methods since the aggregation can be monitored by fluoresence intensity. Other exemplary fusion polypeptides include other fluorescent proteins, or modifications thereof, glutathione S transferase (GST), maltose binding protein, poly His, and the like, or any type of epitope tag. Such fusion polypeptides can be detected, for example, using antibodies specific to the fusion polypeptides. The fusion polypeptides can be an entire polypeptide or a functional portion thereof so long as the functional portion retains desired properties, for example, antibody binding activity of fluorescence activity. Alternatively, antibodies specific for an ataxin-2 polypeptide can be used to monitor a neurodegenerative phenotype such as formation of inclusion bodies, as disclosed herein (see Example IV).

The invention further provides a method of identifying a potential therapeutic agent for use in treating a neurodegenerative disease. The method includes the steps of contacting a cell containing a DNA construct comprising nucleic acid encoding an ataxin-2 polypeptide with a compound; and screening the cell for an improved neurodegenerative phenotype, thereby identifying a potential therapeutic agent for use in treating a neurodegenerative disease. The cell can be isolated from a transgenic non-human mammal having nucleated cells containing the SCA2 DNA construct. Alternatively, the cell can contain a DNA construct comprising a nucleic acid encoding a green fluorescent protein fusion, or other fusion polypeptide, with an ataxin-2 polypeptide.

Cells expressing an ataxin-2 polypeptide can be used in a preliminary screen to identify compounds as potential therapeutic agents having activity that alters a phenotype associated with SCA2 expression, for example, compounds that inhibit formation of inclusion bodies. As with in vivo screens using SCA2 mutant non-human mammals, an appropriate control cell can be used to compare the results of the screen, for example, a control cell not expressing a SCA2 transgene or a control cell expressing a form of SCA2 that does not exhibit a neurodegenerative phenotype such as SCA2(22). The effectiveness of compounds identified by an initial in vitro screen using cells expressing SCA2 can be further tested in vivo using the invention SCA2 mutant non-human mammals, if desired. Thus, the invention provides methods of screening a large number of compounds using a cell-based assay, for example, using high throughput screening, as well as methods of further testing compounds as therapeutic agents in an animal model of neurodegenerative disease.

It is understood that modifications which do not substantially affect the activity of the various embodiments of this invention are also provided within the definition of the invention provided herein. Accordingly, the following examples are intended to illustrate but not limit the present invention.

EXAMPLE I

Localization of Inclusion Bodies in SCA2

This example describes characterization of the localization of inclusion bodies in SCA2 patients and in vitro models of SCA2.

Ataxin-2 was previously reported to have a cytoplasmic localization in three brains from SCA2 patients (Huynh et al., *Ann. Neurol.*, 45:232–241 (1999)). It was possible, however, that ataxin-2 was processed to smaller polyQ-containing fragments that did not include the epitope recognized by the ataxin-2 antibodies used in the previous study. To address this, the 1C2 monoclonal antibody, which recognizes expanded polyQ repeats, was used to determine localization of ataxin-2.

The presence of ataxin-2 fragments was analyzed by western-blot analysis of brain protein extracts from an SCA2 patient, a neurologically normal individual and an Alzheimer patient. Briefly, to examine ataxin-2 expression in these patients, western blot analysis of human cortical brain extracts was performed with antibodies to ataxin-2 peptides (SCA2A and SCA2B) (see FIG. 1), 1C2 (to polyQ domains) and β-actin. Brain protein extracts (100 μg/lane) from an SCA2 patient, normal individual and Alzheimer patient were analyzed. Both ataxin-2 antibodies detected full-length ataxin-2 (145 kD) in all three extracts and a full-length ataxin-2(Q41) (180 kD) in the SCA2 extract. The SCA2A antibody also detected a 42 kD fragment that was recognized by the 1C2 antibody. The SCA2B antibody detected an additional 70 kD protein in all samples.

Western blots were stained with the SCA2A and SCA2B antibodies and compared with the pattern observed by staining the identical extracts with the 1C2 monoclonal antibody. The SCA2A antibody recognized full-length ataxin-2 with the normal (145 kD) and expanded polyQ repeats (180 kD), as well as a 42 kD fragment in the SCA2 patient. The 42 kD protein was barely detectable in normal brain or Alzheimer brain. As expected, the 1C2 antibody recognized the 180 kD fragment but not the 145 kD protein; it also recognized the 42 kD fragment in the SCA2 patient. This fragment was barely detected by the 1C2 antibody in the Alzheimer and control brains. The 1C2 antibody did not detect smaller proteins of significant abundance, indicating that the 42kD protein was the smallest fragment containing an expanded polyQ tract.

To further confirm that the 42 kD fragment was generated preferably by ataxin-2 with an expanded polyQ tract, and to investigate whether mutant ataxin-2 was ubiquitinated, 293T cells were transfected with pEGFP-SCA2(Q22) or pEGFP-SCA2(Q58), followed by treatment with lactacystin for 24 hours to inhibit the proteasomal pathway. Briefly, to generate GFP fusion with SCA2, a full-length SCA2 cDNA including nucleotides 145 to 4,481 (Pulst et al., *Nature Genet.*, 14:269–276 (1996)) was assembled in the pBluescript vector with 22 or 58 CAG repeats. To generate ataxin-2 expression plasmids, the full-length SCA2 cDNA containing either the 22 or 58 CAG repeat was shuttled into the pEGFPC2 (Clontech; Palo Alto Calif.) or pcDNA vectors (Invitrogen; Carlsbad Calif.). These constructs were named pEGFP-SCA22, pEGFP-SCA58, pcDNA-SCA22 or pcDNA-SCA58.

Transient expression of pEGFP-SCA2 constructs was analyzed in 293T cells. To investigate ubiquitination of ataxin-2, 293T cells growing at 60% confluency in 100-mm Petri dishes were transfected with either pEGFP-SCA2 or pcDNA-SCA2 constructs (10 μg) containing either 22 or 58 CAG repeats. Transfected cells were grown overnight and then treated with culture medium with or without lactacystin (10 μM) for 24 h. Cells were incubated with triple detergent buffer (0.5% sodium dodecyl sulfate (SDS), 1% Triton-X 100, 0.5% deoxycholate, 100 mM Tris-HCl, pH 8.0, 150 mM NaCl, and Sigma mammalian protease inhibitors cocktail (Sigma; St. Louis Mo.)) for 1 h on ice with occasional vortexing. Protein extracts were centrifuged at maximum speed in an Eppendorf microfuge at 4° C. for 30 min, and pellets were resuspended in triple detergent buffer. Both protein extract and pellet suspension were stored at −70° C. For western-blot analysis, 100 μg total protein extract per lane was mixed with SDS-polyacrylamide gel electrophoresis (PAGE) sample buffer and incubated for 2 h at 37° C. before loading on to a 4–15% SDS-PAGE gradient gel. Western blots were detected with SCA2A, 1C2 and ubiquitin antibodies.

Western blots were performed on transfected 293 cell protein extracts and insoluble pellets using the GFP or ubiquitin antibody. Untreated cells served as controls. The GFP antibody detected the full-length GFP-ataxin-2 with Q22 and Q58 at 200 kD and an additional band at 70 kD in 293T cells transfected with pEGFP-SCA2(Q58). Neither the 70 kD nor the 200 kD proteins were detected in untransfected 293T protein extracts. The 70 kD protein was not abundant in the pEGFP-SCA2(Q22) transfected cells, indicating that the 42 kD fragment was likely preferably generated from ataxin-2 containing expanded polyQ repeats.

Treatment with lactacystin irreversibly inhibits the proteasomal pathway, resulting in the accumulation of ubiquitin-conjugated protein complexes. Lactacystin-treated cells had increased levels of ubiquitin-conjugated protein complexes and GFP-tagged ataxin-2. The ubiquitin antibody detected a strong smear above 60 kD in protein extracts of lactacystin-treated cells compared with untreated samples, indicating that lactacystin treatment had caused a general increase in ubiquitin-conjugated protein complexes in 293T cells. There were no large aggregates above the p200 band detected by the GFP antibody in either the control or lactacystin-treated cells. Western blots of detergent-insoluble and nuclear proteins from these cells with either GFP or SCA2 antibodies did not detect any additional large protein complexes. The levels of both GFP-ataxin-2(Q22) and GFP-ataxin-2(Q58) fusion proteins were increased in the insoluble fractions of the lactacystin-treated transfected cells, indicating that GFP-ataxin-2 likely decreases ataxin-2 solubility.

To investigate whether the GFP fusion caused any interference with ubiquitin conjugation, 293T cells were transfected with pcDNA-SCA2(Q22) or pcDNA-SCA2(58) and treated with lactacystin. Western blots of these protein extracts with 1C2 or ubiquitin antibodies showed that lactacystin treatment increased the total amount of ataxin-2 (Q58) (p180), but no large ataxin-2 aggregates were found. In the insoluble fractions, ataxin-2(Q58) was faintly detected in both lactacystin-treated and untreated samples, indicating that the full-length ataxin-2(Q58) without GFP fusion was detergent soluble. These results showed that there were no detectable large ubiquitin-conjugated protein complexes formed by mutant ataxin-2, although polyQ expansion resulted in an accumulation of ataxin-2 that was enhanced by lactacystin treatment.

To investigate whether intranuclear inclusion bodies consisting of truncated or ubiquitinated ataxin-2 fragments were abundant in vivo in human SCA2 tissues, antibodies to ataxin-2 (SCA2A), the polyQ tract (1C2) and ubiquitin were used to stain sections from a normal cerebellum and the cerebellum from an SCA2 patient with 58 CAG repeats. Immunohistochemical staining was performed on cerebellar sections from a normal individual and an SCA2 patient with 58 CAG repeats, and the sections were nuclear counterstained with haematoxylin. Purkinje cells were stained with antibodies to ataxin-2 peptides SCA2A, the 1C2 monoclonal antibody to polyQ tracts, and ubiquitin.

The SCA2A antibody staining was strong, punctate and evenly distributed in normal Purkinje cells, as previously shown (Huynh et al., supra, 1999), whereas the 1C2 antibody failed to label any cellular structures. Ubiquitin labelling was undetectable in Purkinje cells and other neurons in both normal and SCA2 brain sections. The same ubiquitin antibody detected Lewy bodies in the midbrain of two patients with sporadic Parkinson disease and a smear banding pattern in the lactacystin-treated 293T cells, confirming that this antibody detects ubiquitin-conjugated protein complexes. Moreover, antibodies to proteasomal subunits did not show enhanced labeling of Purkinje cells or other neurons in SCA2 brain sections. In brain sections from four different SCA2 patients, both the SCA2A and 1C2 antibodies labeled Purkinje cells throughout the cytoplasm, with some granulated cytoplasmic vesicles. The 1C2 antibody did not label normal Purkinje cells but did intensely label large cytoplasmic structures in SCA2 Purkinje cells.

These results show that SCA2 inclusion bodies are located in the cytoplasm and that there is a lack of intranuclear inclusion bodies in SCA2.

EXAMPLE II

Transgenic Mouse Lines Expressing Mutant Human Ataxin-2

This example describes generation of transgenic mouse lines expressing mutant human ataxin-2.

Intranuclear inclusions have been identified in all animal models of human dominant ataxias so far (Reddy et al., Nature Genet., 20:198–202 (1998); Klement et al., Cell, 95:41–53 (1998); Mangiarini et al., Cell, 87:493–506 (1996); Mangiarini et al., Nature Genet., 15:197–200 (1997); Davies et al., Phil. Trans. R. Soc. Lond. B Biol. Sci., 354: 981–989 (1999); Burright et al., Cell, 82:937–948 (1995); Clark et al., J. Neurosci., 17:7385–7395 (1997)). Therefore, the effect of expression of full-length SCA2 cDNA under the control of the Purkinje-cell-specific Pcp2 regulatory element was investigated).

To generate transgenic constructs, the β-galactosidase sequence from the pZ03-β-Gal plasmid, which contains the Pcp2/L7 promoter as well as untranslated and poly(A) sequences of Pcp2, was replaced with the full-length SCA2 sequence (Vandaele et al., Genes Dev., 5:1136–1148 (1991); plasmid provided by H. T. Orr (University of Minnesota, Minneapolis). The correct recombinant plasmids were confirmed by double-stranded sequencing. The transgenic recombinant plasmids were designated pZ03SCA22 (22 CAG repeats) or pZ03SCA58 (58 CAG repeats). To linearize the transgenic construct, the pZ03SCA22 and pZ03SCA58 plasmids were digested with SalI and AatII to generate two bands of 2,188 and 6,451 bp. The 6,451-bp SCA2 transgenic fragment was isolated in a sucrose gradient.

To generate transgenic mouse lines, sucrose gradient purified SCA2 transgenic fragments were microinjected into pronuclei of the B6D2F1 mouse strain, a C57BL/6JxDBA/2J hybrid. Positive founders were backcrossed to wild type of the same hybrid strain. To determine the genotype of transgenic mice, tail DNAs were subjected to PCR using two primer pairs, one pair spanning the CAG-repeat region and the other pair spanning exons 16 and 17 (see below). Using this method, founder lines were identified; 4 human mutant founder lines, Q58-5, Q58-11, Q58-5B and Q58-19 carrying 58 CAG repeats and 2 human wild-type lines, Q22-4 and Q22-5, carrying 22 CAG repeats. Only three Q58 lines, Q58-5B, Q58-11 and Q58-19, were able to produce offspring.

To determine transgene copy number, equal amounts of genomic DNAs from wild-type, Q22 and Q58 mice were digested with RsaI and subjected to quantitative Southern-blot analysis after hybridization with an SCA2 cDNA fragment common to both mouse and human (mouse exon 15).

Three lines expressing ataxin-2(Q58) and two lines expressing ataxin-2(Q22) were evalutated. Quantitative Southern-blot analysis of RsaI-digested DNA showed that there were two transgene copies for line Q58-5B, and three or four copies for lines Q58-11 and Q58-19, whereas lines Q22-4 and Q22-5 had one copy each.

Mouse lines were also characterized with respect to the number of CAG repeats by CAG-repeat PCR analysis. Briefly, at weaning age, a 1-cm piece of tail was cleaved from the animal and DNA was isolated using the Puregene DNA Isolation kit (Gentra Systems; Minneapolis Minn.)). After washing, the precipitate was resuspended in TE buffer (100 µl). Using two primer pairs, tail DNA (50 ng) was analyzed by PCR analysis to identify mice carrying the transgene. One primer pair, 1052A (5'-

GCGTGCGAGCCGGTGTAT-3'; SEQ ID NO:3) and 1190B (5'-CGGGCTTGCGGACATTG-3'; SEQ ID NO:4), was a human-specific primer pair flanking the CAG-repeat region. Step-up PCR conditions were as follows: denaturation for 5 min at 95° C., 5 cycles of denaturation at 95° C. for 1 min 30 sec; annealing at 65° C. for 30 sec, and extension at 72° C. for 1 min, followed by 30 cycles of 95° C., 1 min 30 sec denaturation, 60° C., 30 sec annealing, and 72° C., 1 min extension. This primer pair generates a 145-bp fragment for the 22 CAG SCA2 cDNA and a 258-bp fragment for the 58 SCA2 cDNA. The second primer pair, A40 (5'-GGTTCCTTCTCATCCAACTG-3'; SEQ ID NO:5) and 3' STSB (5'-GATGTGTTCATGACTTTCAAGG-3'; SEQ ID NO:6), flanks intron 16. At standard PCR conditions (35 cycles of 95° C. for 90 sec denaturation, 60° C. for 30 sec annealing, 72° C. for 4 min extension), the A40/3' STSB primer pair generates a 424-bp amplicon for the SCA2 transgene and a 1,424-bp amplicon for the endogenous gene (including intron 16).

In contrast to human expanded SCA2 CAG repeats, which are unstable and continue to expand in succeeding generations (Pulst et al., *Nature Genet.*, 14:269–276 (1996)), 45 offspring in 3 generations of the Q58-11 line transmitted the transgene stably.

To determine whether the transgenes were expressed, RNA and protein were extracted from cerebella of transgenic lines. mRNA was reverse transcribed into single-strand DNA using RT-PCR. Briefly, for RT-PCR and RNA isolation, mouse cerebella were homogenized in Tri-solve Reagent (Life Technologies; Rockville Md.) and total RNAs were isolated as described in the manufacturer's protocol. Total RNAs were selectively recitative with 3.75 M LiCl/25 mM EDTA to remove trace genomic DNA contamination. The first-strand cDNA for RT-PCR was synthesized from total RNA (2 µg) using the Promega RT-PCR System (Promega; Madison Wis.). An aliquot of the reaction was subjected to PCR using human-specific primer pairs spanning the CAG tract.

Cerebella from a wild-type, line Q22-5, or line Q58-11 mouse were subjected to RT-PCR using a human-specific primer pair (A1-B1) flanking the CAG repeat. The A1 (51'-GGGCCCCTCACCATGTCG-3'; SEQ ID NO:9) and B1 (5'-CGGGCTTGCGGACATTGG-3'; SEQ ID NO:10) primers have been previously described (Pulst et al., *Nature Genetics* 14:269–276 (1996)). The A1-B1 primer pair generated a 126-bp amplicon containing 22 CAG repeats in the Q22-5 line and a 162-bp amplicon containing 58 CAG repeats in the Q58-11 line. The 126-bp and 162-bp fragments were also observed in the positive control PCR reaction containing either the transgenic constructs pZ03-SCA2(Q22) or pZ03-SCA2(Q58). Amplicons were compared to HaeIII digested φX174RFDNA marker. Cerebella of transgenic mice, but not of wild-type mice contained transgene mRNA with either $CAG_{22}$ or $CAG_{58}$.

Western-blot analysis of protein extracts isolated from the cerebella of Q58-11 mice demonstrated expression of the trans-genes at the protein level. Mouse protein extracts were probed with the SCA2A antibody using western blot analysis. Cerebella (including brainstems) from wild-type, heterozygous Q58-11, or homozygous Q58-11 animals were homogenized in triple-detergent buffer and 100 µg of the total protein were loaded in each lane. The SCA2-A antibody detected full-length ataxin-2 and a 39 kD protein fragment in all extracts. A weak 180 kD band was detected in the heterozygous mouse protein extract. The 180 kD band was more intense in the homozygous mouse brain extract.

A 180 kD protein was detected in the cerebella from Q58-11 heterozygous and homozygous mice with the expected increased expression in homozygous animals. This band was not detected in wild-type animals. Several proteins of smaller molecular weight were seen in wild-type and transgenic lines, indicating that they likely were mouse endogenous proteins. In tissue sections, the 1C2 antibody labeled Purkinje neurons from lines Q58-5B, Q58-11 and Q58-19, confirming that these lines expressed the human transgene.

To further determine the relative expression levels of the ataxin-2 transgenes, RT-PCR was performed on total RNA isolated from cerebella of wild-type and transgenic lines. To compare the expression levels of the transgene from different lines, PCR was performed using primers 3014A (5'-TTACAGCCAAGTCTACTCTGAA-3'; SEQ ID NO:7) and 3258B (5'-AGTCTGAACCCCTTGGGAA-3'; SEQ ID NO:8), which span exon 15 and generate a 266-bp amplicon of the endogenous mouse transcript and a 260-bp amplicon from the transgene transcript. The primer pair 3014A/3258B amplifies the transgene slightly more efficiently due to two mismatches with the mouse sequence. To facilitate separation of the mouse and the human amplicons, the PCR product was digested with MseI (New England BioLabs; Beverly Mass.). Fragments were separated in 3% Tris-borate-EDTA (TBE) METAPHOR agarose (BioWhittaker Molecular Applications; Rockland Me.). The human and mouse PCR products can be differentiated after digestion with MseI, which cleaves only the endogenous mouse 266-bp PCR product into two fragments of 79 bp and 187 bp.

Relative expression of transgenes was compared with endogenous ataxin-2 expression levels using RT-PCR. Wild type, heterozygote Q22-4, heterozygote Q22-5, heterozygote and homozygote Q58-5B, heterozygote and homozygote Q58-11, and heterozygote and homozygote Q58-19 were analyzed. RNase treatment resulted in loss of all amplicons.

Line Q22-4 had a slightly higher transgene expression than line Q22-5 at levels comparable with heterozygote animals in lines Q58-5B and Q58-19. Transgene expression in line Q58-11 was the highest of all lines. These experiments also demonstrated that transgene expression levels in homozygous animals were higher than those in their heterozygous counterparts.

A SCA2 transgenic mouse line expressing 70–80 polyglutamines is being generated. The mouse line is screened essentially as described above and below.

These results describe the generation and characterization of transgenic mice expressing human SCA2 and mutant forms thereof.

EXAMPLE III

Functional Testing of Transgenic Mouse Lines Expressing Human SCA2

This example describes functional characterization of SCA2 transgenic mouse lines.

Three independent functional tests were carried out to determine the effect of transgene expression on Purkinje-cell function: clasping, footprinting and rotarod analysis.

Mice with neurodegenerative phenotypes have a tendency to fold their hindlegs when held by the tail for at least one minute. For the clasping test, mice were held by the tail for one minute. When the mouse folded both hindlegs close to the body, it received a score of 100. If only one leg was folded, it received a score of 50. Mice within one week of birth were grouped into a single test group.

Clasping was observed at 16–20 weeks in line Q58-19 and at 8–12 months in the Q58-11 line. In Q58-5B animals, no clasping was observed up to 26 weeks of age. Q22-4 and Q22-5 animals did not show clasping up to 12 months.

Footprinting analysis was also performed. To measure stride length, the left foot was painted with red aqueous ink and the right foot with black ink, and the mouse was allowed to run through a dark 40 cm×8cm×6cm (L×W×H) tunnel. The total stride length value obtained from each animal was an average of the stride length from the total number of steps produced by each leg. Hindleg footprints at 8 and 16 weeks were measured and compared between animals matched for age and weight.

Stride length was altered in mice expressing mutant ataxin-2 compared with that of wild-type mice or mice expressing ataxin-2(Q22) (FIG. 2a). The mouse lines designated wtQ58-5B, wtQ58-19 and wtQ58-11 denote wild-type mice matched with the respective transgenic lines. Progressive functional loss was observed in lines Q58-5B, Q58-11 and Q58-19. Footprint analysis showed progressive reduction in stride length for all three lines examined at 8 and 16 weeks (FIG. 2a; n=11–14 animals per data point). In the Q58-19 line, stride length was reduced by 19% at 8 weeks (P <0.0001, 2-way ANOVA). At 16 weeks, all threee Q58 lines showed similar reduction in stride length (P 0.001, 2-way ANOVA). Animals expressing ataxin-2(Q22) have the same stride length as wild-type animals, even when examined at 12 months (FIG. 2a).

Rotarod performance of wild type and Q58-11 mice was analyzed. To measure motor coordination and balance, mice were tested using Basile Rotarod treadmills (Stoelting Co.; Wood Dale Ill.). This test has been used to assess functional impairment in mice carrying SCA1 and huntingtin transgenes (Reddy et al., *Nature Genet.*, 20:198–202 (1998); Klement et al., *Cell*, 95:41–53 (1998); Clark et al., *J. Neurosci.*, 17:7385–7395 (1997)). Mice were placed on an accelerating rod with a rotating speed from 4 to 40 r.p.m. for a maximum of 10 min with a minimum inter-trial interval of 15 min, and the time spent on the rod without falling was recorded. The duration of the test was 4 days with 4 individual trials per day.

Rotarod testing of lines Q58-11 and Q58-5B confirmed functional deficits. Rotarod analysis of mice from line Q58-11 is shown in FIG. 2b. The graph shows average performance on the rotarod apparatus of four trials each day on four consecutive days. Differences were significant for homozygous Q58-11 mice at 16 and at 26 weeks (2-way ANOVA compared with wild type, P<0.0001), and for heterozygous Q58-11 mice at 26 weeks (P<0.0001). Numbers in parentheses indicate number of animals tested.

Wild-type, heterozygous and homozygous Q58-11 mice were tested at 6, 14–16 and 26 weeks. At six weeks, motor performance of transgenic animals was not different from that of wild-type mice. At 16 weeks, homozygous Q58-11 mice already performed poorly on rotarod testing (P<0.001, 2-way ANOVA), whereas heterozygous Q58-11 animals performed as well as wild type (FIG. 2b). Although mice from the Q58-5B line exhibited later stride-length deficits than those from the Q58-11 line, their rotarod performance matched that of the Q58-11 mice. The functional deficits were progressive. At 26 weeks, both heterozygous and homozygous Q58-11 animals showed severely impaired motor performance. The rotarod performance of animals expressing ataxin-2(Q22) was not significantly different from that of wild-type animals.

These results show functional neurodegenerative phenotypes in transgenic mice expressing human SCA2 having a 58 polyglutamine repeat.

EXAMPLE IV

Anatomic Changes in Transgenic Mouse Lines Expressing Human SCA2

This example describes morphological characterization of SCA2 transgenic mouse lines.

The SCA2 transgene is under the control of the Purkinje cell specific regulatory element Pcp2. To investigate morphological changes in Purkinje cells, calbindin-28K immunoreactivity in tissue sections from heterozygous animals at 27 weeks was compared with that from wild-type mice. Calbindin-28K is a protein specifically expressed in cytoplasm and dendritic processes of cerebellar Purkinje cells.

Histological examination and immunohistochemistry was performed on Purkinje cells from wild type and SCA2 transgenic mice. To determine whether Q58 transgenic mice exhibited Purkinje cell loss, both calbindin-28K-positive and calbindin-28K-negative Purkinje cells were counted from wild-type and Q58 transgenic mice at different ages. The percentage of surviving Purkinje cells were obtained by dividing the average number of Purkinje cells obtained from at least two different Q58 animals at the same age with the average number of Purkinje cells from seven wild-type animals.

For comparison to human SCA2 patients, human brain tissues obtained at necropsy were fixed in 10% formalin within 24 h of death, and selected samples were embedded in paraffin. Sections (6 $\mu$m) were cut and mounted onto Superplus microscopic slides (Fisher Scientific; Pittsburgh Pa.). The sections were rehydrated by rinsing twice at 5 min intervals in xylene, 100% ethanol, 95% ethanol and 70% ethanol. After deparaffinization, sections were treated with a protease cocktail, blocked with avidin/biotin and 3% normal goat serum.

For immunohistochemistry, sections were incubated with 10–20 $\mu$g/ml of affinity-purified ataxin-2 antibodies overnight at 4° C. The other antibodies used were as follows: ubiquitin (Dako; Carpinteria Calif.), 1C2 and calbindin D-28K (Chemicon; Temecula Calif.). Primary antibodies were detected using the Vector rabbit ABC elite Peroxidase kit (Vector Laboratories; Burlingame Calif.), enhanced by DAB enhancer, and visualized with diaminobenzidine (DAB; Biomeda; Foster City Calif.). The sections were counterstained with aqueous haematoxylin (Zymed; South San Francisco Calif.). Controls consisted of antibodies pre-absorbed with 100 $\mu$M of the respective peptide and pre-immune sera at comparable concentrations (1/500). For direct comparison, all slides were processed in a single batch to minimize variability.

Calbindin-28K labeling of cerebella was determined in heterozygous Q58-5B, Q58-11, and Q58-19 animals at 27 weeks, and wild-type and homozygous Q58-11 mice at 4 weeks, 7 weeks and 14 weeks. Calbindin-28K labeling of cerebella was also performed on a 7-week Q22-5 mouse section, a human cerebellum from an age-matched normal individual, and a Q41-SCA2 patient for direct comparison.

Changes in calbindin-28K labeling were seen as early as four weeks but became more pronounced with age. Most Purkinje cells lost calbindin-28K immunoreactivity in mice from lines Q58-5B and Q58-11, whereas loss in line Q58-19 was more discreet. Calbindin-28K loss was progressive). At four weeks, calbindin-28K labeling was strong in Q22 mice and wild-type animals, whereas calbindin-28K immunoreactivity was already reduced in Purkinje cell bodies of homozygous Q58-11 mice. From 7 to 14 weeks, further loss of calbindin-28K immunoreactivity was observed compared with wild-type animals and Q22 transgenic mice. The loss of calbindin-28K immunoreactivity in Purkinje cells of Q58-11 mice was similar to that observed in human Purkinje neurons from an SCA2 patient with 41 SCA2 CAG repeats. Loss of the dendritic arbour was closely followed by a loss in Purkinje cell number. The percentage of surviving Purkinje cells showed a progressive decline. At 24–27 weeks, Purkinje cell number was reduced by 50–53% in lines Q58-5B, Q58-11 and Q58-19. Compared with wild-type mice, mice expressing ataxin-2(Q22) showed no reduction in Purkinje cell number, even at one year of age.

Expression and localization of ataxin-2 in Purkinje cells was determined. Paraffin-embedded mouse brain sections from wild-type, Q58-11, Q58-19 and Q58-5B mice were stained with the SCA2A, 1C2 or ubiquitin antibody and counterstained with haematoxylin.

Cytoplasmic accumulation of ataxin-2 immunoreactivity and a lack of nuclear localization in Purkinje cells was observed in the Q58 mouse cerebella. Labeling with either the SCA2A or the 1C2 antibody did not reveal intranuclear inclusions. Purkinje cells from all three Q58 transgenic lines labeled intensely with the SCA2A and 1C2 antibodies. The SCA2A staining was more intense than in wild-type Purkinje cells and located throughout the cytoplasm with some granulated cytoplasmic vesicles. The 1C2 staining consisted of cytoplasmic microaggregates. Ubiquitin labeling was undetectable in Purkinje cells of wild-type and transgenic animals.

As described in Example II, there is evidence of truncation of ataxin-2 in both western blots of brain extracts and cultured cells transfected with full-length ataxin-2(Q58). The truncated 42 kDa fragment contains the polyQ tract, but the 42 kDa form does not enter the nucleus, even when this fragment is overexpressed. Based on the recognition of the 42 kDa fragment by the 1C2 antibody on western blots, the presence of the 42 kDa fragment was not observed in the nucleus of Purkinje cells of patients with SCA2.

Although all three antibodies used in this study showed cytoplasmic staining, the SCA2-A and SCA2-B antibodies, which preferentially recognize full-length normal and mutated ataxin-2, yielded a more diffuse cytoplasmic staining, whereas the 1C2 antibody detected microaggregates. It has been suggested that truncated proteins serve as a nidus for the formation of intranuclear aggregates and recruitment of full-length proteins (Scherzinger et al., *Cell*, 90:549–558 (1997)). The staining pattern observed in SCA2 brains is consistent with a similar mechanism for cytoplasmic aggregation. These studies emphasize the location of the initial toxic event in the cytoplasm. However, other factors can be involved, including the initiation of cell dysfunction and eventual death remain. Because caspase cleavage appears to be important in cellular models of polyQ-induced apoptosis (Sanchez et al., *Neuron*, 22:623–633 (1999); Kim, et al., *J. Neurosci.*, 19:964–973 (1999); Wellington et al., *J. Biol. Chem.*, 273:9158–9167 (1998)), these mouse models using full-length cDNA constructs are useful for testing the importance of caspase cleavage in vivo. In human SCA2 brains, the abundance of the 42-kD ataxin-2 fragment appears to be increased compared with that of normal brains, although it is not yet known whether this truncation event is important for SCA2 pathogenesis.

The targeting of transgene expression to a specific neuronal population using the Purkinje cell-specific promoter facilitates evaluation of functional and anatomical consequences of the expression of SCA2. The PcP2 promoter has now been used for the expression of ataxins 1, 2 and 3 with different results. Functional deficits and neuronal changes were only detected when ataxin-3 was severely truncated (Ikeda et al., *Nature Genet.*, 13:196–202 (1996)), although direct comparisons with other models are limited due to different expression levels of transgenes.

Mice expressing ataxin-1(Q82) and ataxin-2(Q58) share similar functional and morphological features. When adjustments are made for different polyQ lengths, the similarity in the time course of pathological changes is striking. In both models, the functional impairment is mirrored by changes in the Purkinje-cell dendritic tree as visualized by altered calbindin-28K staining. Changes are dosage dependent, and homozygous mice are affected significantly earlier than heterozygous animals (Burright et al., *Cell*, 82:937–948 (1995); Clark et al., *J. Neurosci.*, 17:7385–7395 (1997); Vig et al., *Neurology*, 50:106–113 (1998)). Both ataxin models show evidence of neurodegeneration, although cell loss occurs much later than the onset of functional deficits. This pattern follows observations in human brains in that Purkinje cell atrophy in human hereditary ataxia begins with dendritic loss and then proceeds to the complete destruction of the cell body (Koeppen, *J. Neuropathol. Exp. Neurol.*, 50:505–514 (1991)).

Despite these functional and morphological similarities between SCA1 and SCA2 transgenic lines, the site of the initiation of pathology appears to be different. In SCA1, nuclear localization is essential for pathogenesis, although intranuclear aggregation is not. The results described above show that neither normal nor mutant ataxin-2 acquire a nuclear localization. This holds true for mouse models, cultured cells, and human Purkinje cells. The presence of fragments containing truncated polyQ were also not found in the nucleus. Although other investigators have detected occasional intranuclear aggregates in human SCA2 brains, these were never seen in Purkinje cells (Koyano et al., *Neurosci. Lett.*, 273:117–120 (1999)).

Previous results in cultured mouse and human neurons had suggested that ubiquitination and subsequent degradation by the proteasome machinery is possibly common to all polyQ proteins, independent of their nuclear or cytoplasmic localization (Cummings et al., *Nature Genet.*, 19:148–154 (1998); Cummings et al., *Neuron*, 24:879–892 (1999); Chai et al., *Hum. Mol. Genet.*, 8:673–682 (1999)). Ataxin-2 and possibly ataxin-6 appear to break this mold, at least with regard to detectable ubiquitination of aggregated or accumulated mutant proteins. In human SCA6 brains, ataxin-6 was not labeled by anti-ubiquitin antibodies (Ishikawa et al., *Hum. Mol. Genet.*, 8:1185–1193 (1999)). In SCA2 human brains as well as in brains from transgenic mouse lines, no increase in the ubiquitination of ataxin-2 was detectable, despite the presence of large amounts of immunoreactive ataxin-2 in the cytoplasm. In cultured cells, lactacystin-treated transfected cells did not produce ubiquitin-conjugated ataxin-2(58) complexes of high molecular weight, although the level of mutant ataxin-2 was increased in these cells. Ataxin-2(Q58) remained soluble, unlike ataxin-1 (Cummings et al., *Neuron*, 24:879–892 (1999)).

Expression studies of GFP linked to the pll5 Golgi/ER trans-ported protein led to the description of an aggresome complex that contained soluble, non-ubiquitinated proteins in its center, although proteasome proteins and other chaperons were recruited into the aggresomes (Garcia-Mata et al., *J. Cell Biol.*, 146:1239–1254 (1999)). This contrasts with another class of aggresomes that involves the cytoplasmic aggregation and degradation of misfolded and ubiquitinated transmembrane proteins such as presenilin-1 or the cystic fibrosis transmembrane conductance regulator (Johnston et al., *J. Cell Biol.*, 143:1883–1898 (1998). Overexpression of the GFP-p115 chimaera caused incorrect Golgi localization, but with a normal ER-Golgi transport of the p115 protein. In these studies, non-Golgi localization of ataxin-2 with expanded polyQ repeats was observed in cell culture. This observation, along with the observed accumulation of ataxin-2 in human SCA2 neurons, together with the fact that wild-type ataxin-2 and its interactor (A2BP1) (Shibata et al., *Hum. Mol. Genet.*, 9:130–1313 (2000)) are both Golgi proteins, support the model that ataxin-2 is not ubiquitinated and degraded like other polyQ proteins.

These results show morphological neurodegenerative phenotypes are exhibited in transgenic mice expressing human SCA2 having a 58 polyglutamine repeat. These results also demonstrate that intranuclear localization is not necessary for all classes of polyQ pathogenesis or for disease progression. The finding that cytoplasmic localization and microaggregation or accumulation of ataxin-2 cause Purkinje cell pathogenesis places SCA2 into the larger group of neurodegenerative diseases where protein aggregation occurs in the cytoplasm, for example, Parkinson disease, Alzheimer disease, and SCA6 (Mezey et al., *Mol. Psychiatry*, 3:493–499 (1998); Lippa et al., *Am. J. Pathol.*, 153:1365–1370 (1998); Ishikawa et al., *Hum. Mol. Genet.*, 8:1185–1193 (1999)). Therefore, the SCA2(58) transgenic mouse can function as an animal model for other neurodegenerative diseases, including studies to characterize similarities and differences in neurodegenerative diseases involving cytoplasmic versus nuclear aggregation mechanisms.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

What is claimed is:

1. A transgenic mouse comprising cells containing a DNA sequence encoding an ataxin-2 polypeptide comprising a polyglutamine tract of about 58 glutamines, said sequence operatively linked to a Purkinje cell-specific promoter, wherein said mouse exhibits a neurodegenerative phenotype selected from the group consisting of developing a reduced number of Purkinje cells compared to a wild-type mouse and impaired motor function compared to a wild-type mouse.

2. The transgenic mouse of claim 1, wherein said mouse is homozygous for said transgene.

3. The transgenic mouse of claim 1, wherein said mouse is heterozygous for said transgene.

4. A method of identifying a therapeutic agent for use in treating a neurodegenerative disease, comprising:
   (a) administering a compound to the transgenic mouse of claim 1, and
   (b) screening said transgenic mouse for an improved neurological response associated with a neurodegenerative phenotype of said transgenic mouse, thereby identifying a therapeutic agent for use in treating said neurodegenerative disease.

5. The method of claim 4, wherein said mouse is homozygous for said transgene.

6. The method of claim 4, wherein said mouse is heterozygous for said transgene.

7. A cell isolated from the transgenic mouse of claim 1, wherein said cell expresses said ataxin-2 polypeptide comprising a polyglutamine tract of about 58 glutamines.

8. The mouse cell of claim 7, wherein said mouse is homozygous for said transgene.

9. The mouse cell of claim 7, wherein said mouse is heterozygous for said transgene.

10. A method of identifying a potential therapeutic agent for use in treating a neurodegenerative disease, comprising:
    (a) contacting a cell of claim 7, said cell containing a DNA construct comprising a DNA sequence encoding an ataxin-2 polypeptide having a polyglutamine tract of about 58 glutamines, with a compound, and
    (b) screening said cell to identify a compound having activity that alters a phenotype associated with ataxin-2 polypeptide expression, thereby identifying a potential therapeutic agent for use in treating said neurodegenerative disease.

11. The method of claim 10, wherein said DNA construct comprises a DNA sequence encoding a green fluorescent protein fusion with said ataxin-2 polypeptide.

12. A transgenic mouse comprising cells containing a DNA sequence encoding an ataxin-2 polypeptide comprising a polyglutamine tract of about 58 glutamines, said sequence operatively linked to a Purkinje cell-specific promoter, wherein said mouse develops a reduced number of Purkinje cells compared to a wild-type mouse.

13. The transgenic mouse of claim 10, wherein said mouse is homozygous for said transgene.

14. The transgenic mouse of claim 13, wherein said mouse is heterozygous for said transgene.

15. A method of identifying a therapeutic agent for use in treating a neurodegenerative disease, comprising:
    (a) administering a compound to the transgenic mouse of claim 12, and
    (b) screening said transgenic mouse for an improved neurological response associated with a neurodegenerative phenotype of said transgenic mouse, thereby identifying a therapeutic agent for use in treating said neurodegenerative disease.

16. The method of claim 15, wherein said mouse is homozygous for said transgene.

17. The method of claim 15, wherein said mouse is heterozygous for said transgene.

18. A cell isolated from the transgenic mouse of claim 12, wherein said cell expresses said ataxin-2 polypeptide comprising a polyglutamine tract of about 58 glutamines.

19. The cell of claim 18, wherein said mouse is homozygous for said transgene.

20. The cell of claim 18, wherein said mouse is heterozygous for said transgene.

21. A method of identifying a potential therapeutic agent for use in treating a neurodegenerative disease, comprising:
    (a) contacting a cell of claim 18, said cell containing a DNA construct comprising a DNA sequence encoding an ataxin-2 polypeptide having a polyglutamine tract of about 58 glutamines, with a compound, and
    (b) screening said cell to identify a compound having activity that alters a phenotype associated with ataxin-2 polypeptide expression, thereby identifying a potential therapeutic agent for use in treating said neurodegenerative disease.

22. The method of claim 21, wherein said DNA construct comprises a DNA sequence encoding a green fluorescent protein fusion with said ataxin-2 polypeptide.

23. A transgenic mouse comprising cells containing a DNA sequence encoding an ataxin-2 polypeptide comprising a polyglutamine tract of about 58 glutamines, said sequence operatively linked to a Purkinje cell-specific promoter, wherein said mouse exhibits impaired motor function compared to a wild-type mouse.

24. The transgenic mouse of claim 23, wherein said mouse is homozygous for said transgene.

25. The transgenic mouse of claim 23, wherein said mouse is heterozygous for said transgene.

26. A method of identifying a therapeutic agent for use in treating a neurodegenerative disease, comprising:
    (a) administering a compound to the transgenic mouse of claim 23, and
    (b) screening said transgenic mouse for an improved neurological response associated with a neurodegenerative phenotype of said transgenic mouse, thereby identifying a therapeutic agent for use in treating said neurodegenerative disease.

27. The method of claim 26, wherein said mouse is homozygous for said transgene.

28. The method of claim 26, wherein said mouse is heterozygous for said transgene.

29. A cell isolated from the transgenic mouse of claim 23, wherein said cell expresses said ataxin-2 polypeptide comprising a polyglutamine tract of about 58 glutamines.

30. The cell of claim 29, wherein said mouse is homozygous for said transgene.

31. The cell of claim 29, wherein said mouse is heterozygous for said transgene.

32. A method of identifying a potential therapeutic agent for use in treating a neurodegenerative disease, comprising:

(a) contacting a cell of claim 31, said cell containing a DNA construct comprising a DNA sequence encoding an ataxin-2 polypeptide having a polyglutamine tract of about 58 glutamines, with a compound, and (b) screening said cell to identify a compound having activity that alters a phenotype associated with ataxin-2 polypeptide expression, thereby identifying a potential therapeutic agent for use in treating said neurodegenerative disease.

33. The method of claim 32, wherein said DNA construct comprises a DNA sequence encoding a green fluorescent protein fusion with said ataxin-2 polypeptide.

34. A DNA construct comprising a DNA sequence encoding a human ataxin-2 polypeptide, said ataxin-2 polypeptide having a polyglutamine tract comprising about 58 glutamines, operationally linked to a Purkinje cell-specific expression element.

35. A vector comprising the DNA construct of claim 34.

36. An isolated mouse cell comprising the DNA construct of claim 34.

37. A DNA construct comprising a DNA sequence encoding a fusion polypeptide of human ataxin-2 polypeptide and green fluorescent protein, said ataxin-2 polypeptide having a polyglutamine tract comprising about 58 glutamines, operationally linked to a Purkinje cell-specific expression element.

38. The DNA construct of claim 37, wherein said human ataxin-2 polypeptide comprises the amino acid sequence referenced as SEQ ID NO:2.

39. A mouse embryonic stem cell containing a DNA construct comprising a DNA sequence encoding an ataxin-2 polypeptide having a polyglutamine tract of about 58 glutamines, said sequence operatively linked to a Purkinje cell-specific promoter, and said ataxin-2 polypeptide expressed in said embryonic stem cell.

* * * * *

SEQUENCE LISTING

<160> NUMBER OF SEQ ID NOS: 12

<210> SEQ ID NO 1
<211> LENGTH: 4481
<212> TYPE: DNA
<213> ORGANISM: Homo sapien
<220> FEATURE:
<221> NAME/KEY: CDS
<222> LOCATION: (163)...(4099)

<400> SEQUENCE: 1

```
accccgaga   aagcaaccca   gcgcgccgcc   cgctcctcac   gtgtccctcc   cggcccggg         60 gccacctcac   gttctgcttc   cgtctgaccc   ctccgacttc   cggtaaagag   tccctatccg      120
cacctccgct   cccaccggc    gcctcggcgc   gcccgccctc   cg atg cgc tca gcg            174
                                                      Met Arg Ser Ala
                                                        1 gcc gca gct cct cgg agt ccc gcg gtg gcc acc gag tct cgc cgc ttc              222
Ala Ala Ala Pro Arg Ser Pro Ala Val Ala Thr Glu Ser Arg Arg Phe
  5                  10                  15                  20 gcc gca gcc agg tgg ccc ggg tgg cgc tcg ctc cag cgg ccg gcg cgg              270
Ala Ala Ala Arg Trp Pro Gly Trp Arg Ser Leu Gln Arg Pro Ala Arg
                 25                  30                  35 cgg agc ggg cgg ggc ggc ggt ggc gcg gcc ccg gga ccg tat ccc tcc              318
Arg Ser Gly Arg Gly Gly Gly Gly Ala Ala Pro Gly Pro Tyr Pro Ser
             40                  45                  50 gcc gcc cct ccc ccg ccc ggc ccc ggc ccc cct ccc tcc cgg cag agc              366
Ala Ala Pro Pro Pro Pro Gly Pro Gly Pro Pro Pro Ser Arg Gln Ser
         55                  60                  65 tcg cct ccc tcc gcc tca gac tgt ttt ggt agc aac ggc aac ggc ggc              414
Ser Pro Pro Ser Ala Ser Asp Cys Phe Gly Ser Asn Gly Asn Gly Gly
     70                  75                  80 ggc gcg ttt cgg ccc ggc tcc cgg cgg ctc ctt ggt ctc ggg ggg cct              462
Gly Ala Phe Arg Pro Gly Ser Arg Arg Leu Leu Gly Leu Gly Gly Pro
 85                  90                  95                 100 ccc cgc ccc ttc gtc gtc gtc ctt ctc ccc ctc gcc agc ccg ggc gcc              510
Pro Arg Pro Phe Val Val Val Leu Leu Pro Leu Ala Ser Pro Gly Ala
                105                 110                 115
```

```
cct ccg gcc gcg cca acc cgc gcc tcc ccg ctc ggc gcc cgt gcg tcc       558
Pro Pro Ala Ala Pro Thr Arg Ala Ser Pro Leu Gly Ala Arg Ala Ser
        120                 125                 130 ccg ccg cgt tcc ggc gtc tcc ttg gcg cgc ccg gct ccc ggc tgt ccc       606
Pro Pro Arg Ser Gly Val Ser Leu Ala Arg Pro Ala Pro Gly Cys Pro
        135                 140                 145 cgc ccg gcg tgc gag ccg gtg tat ggg ccc ctc acc atg tcg ctg aag       654
Arg Pro Ala Cys Glu Pro Val Tyr Gly Pro Leu Thr Met Ser Leu Lys
150                 155                 160 ccc cag cag cag cag cag cag cag caa cag cag cag caa cag               702
Pro Gln Gln Gln Gln Gln Gln Gln Gln Gln Gln Gln Gln Gln
165                 170                 175                 180 cag cag cag cag cag cag cag ccg ccg ccc gcg gct gcc aat gtc cgc       750
Gln Gln Gln Gln Gln Gln Gln Pro Pro Pro Ala Ala Ala Asn Val Arg
                185                 190                 195 aag ccc ggc ggc agc ggc ctt cta gcg tcg ccc gcc gcc gcg cct tcg       798
Lys Pro Gly Gly Ser Gly Leu Leu Ala Ser Pro Ala Ala Ala Pro Ser
        200                 205                 210 ccg tcc tcg tcc tcg gtc tcc tcg tcc tcg gcc acg gct ccc tcc tcg       846
Pro Ser Ser Ser Ser Val Ser Ser Ser Ser Ala Thr Ala Pro Ser Ser
        215                 220                 225 gtg gtc gcg gcg acc tcc ggc ggc ggg agg ccc ggc ctg ggc aga ggt       894
Val Val Ala Ala Thr Ser Gly Gly Gly Arg Pro Gly Leu Gly Arg Gly
230                 235                 240 cga aac agt aac aaa gga ctg cct cag tct acg att tct ttt gat gga       942
Arg Asn Ser Asn Lys Gly Leu Pro Gln Ser Thr Ile Ser Phe Asp Gly
245                 250                 255                 260 atc tat gca aat atg agg atg gtt cat ata ctt aca tca gtt gtt ggc       990
Ile Tyr Ala Asn Met Arg Met Val His Ile Leu Thr Ser Val Val Gly
                265                 270                 275 tcc aaa tgt gaa gta caa gtg aaa aat gga ggt ata tat gaa gga gtt      1038
Ser Lys Cys Glu Val Gln Val Lys Asn Gly Gly Ile Tyr Glu Gly Val
        280                 285                 290 ttt aaa act tac agt ccg aag tgt gat ttg gta ctt gat gcc gca cat      1086
Phe Lys Thr Tyr Ser Pro Lys Cys Asp Leu Val Leu Asp Ala Ala His
        295                 300                 305 gag aaa agt aca gaa tcc agt tcg ggg ccg aaa cgt gaa gaa ata atg      1134
Glu Lys Ser Thr Glu Ser Ser Ser Gly Pro Lys Arg Glu Glu Ile Met
        310                 315                 320 gag agt att ttg ttc aaa tgt tca gac ttt gtt gtg gta cag ttt aaa      1182
Glu Ser Ile Leu Phe Lys Cys Ser Asp Phe Val Val Val Gln Phe Lys
325                 330                 335                 340 gat atg gac tcc agt tat gca aaa aga gat gct ttt act gac tct gct      1230
Asp Met Asp Ser Ser Tyr Ala Lys Arg Asp Ala Phe Thr Asp Ser Ala
                345                 350                 355 atc agt gct aaa gtg aat ggc gaa cac aaa gag aag gac ctg gag ccc      1278
Ile Ser Ala Lys Val Asn Gly Glu His Lys Glu Lys Asp Leu Glu Pro
        360                 365                 370 tgg gat gca ggt gaa ctc aca gcc aat gag gaa ctt gag gct ttg gaa      1326
Trp Asp Ala Gly Glu Leu Thr Ala Asn Glu Glu Leu Glu Ala Leu Glu
        375                 380                 385 aat gac gta tct aat gga tgg gat ccc aat gat atg ttt cga tat aat      1374
Asn Asp Val Ser Asn Gly Trp Asp Pro Asn Asp Met Phe Arg Tyr Asn
        390                 395                 400 gaa gaa aat tat ggt gta gtg tct acg tat gat agc agt tta tct tcg      1422
Glu Glu Asn Tyr Gly Val Val Ser Thr Tyr Asp Ser Ser Leu Ser Ser
405                 410                 415                 420 tat aca gtg ccc tta gaa aga gat aac tca gaa gaa ttt tta aaa cgg      1470
Tyr Thr Val Pro Leu Glu Arg Asp Asn Ser Glu Glu Phe Leu Lys Arg
                425                 430                 435
```

-continued

| | |
|---|---|
| gaa gca agg gca aac cag tta gca gaa gaa att gag tca agt gcc cag<br>Glu Ala Arg Ala Asn Gln Leu Ala Glu Glu Ile Glu Ser Ser Ala Gln<br>440 445 450 | 1518 |
| tac aaa gct cga gtg gcc ctg gaa aat gat gat agg agt gag gaa gaa<br>Tyr Lys Ala Arg Val Ala Leu Glu Asn Asp Asp Arg Ser Glu Glu Glu<br>455 460 465 | 1566 |
| aaa tac aca gca gtt cag aga aat tcc agt gaa cgt gag ggg cac agc<br>Lys Tyr Thr Ala Val Gln Arg Asn Ser Ser Glu Arg Glu Gly His Ser<br>470 475 480 | 1614 |
| ata aac act agg gaa aat aaa tat att cct cct gga caa aga aat aga<br>Ile Asn Thr Arg Glu Asn Lys Tyr Ile Pro Pro Gly Gln Arg Asn Arg<br>485 490 495 500 | 1662 |
| gaa gtc ata tcc tgg gga agt ggg aga cag aat tca ccg cgt atg ggc<br>Glu Val Ile Ser Trp Gly Ser Gly Arg Gln Asn Ser Pro Arg Met Gly<br>505 510 515 | 1710 |
| cag cct gga tcg ggc tcc atg cca tca aga tcc act tct cac act tca<br>Gln Pro Gly Ser Gly Ser Met Pro Ser Arg Ser Thr Ser His Thr Ser<br>520 525 530 | 1758 |
| gat ttc aac ccg aat tct ggt tca gac caa aga gta gtt aat gga ggt<br>Asp Phe Asn Pro Asn Ser Gly Ser Asp Gln Arg Val Val Asn Gly Gly<br>535 540 545 | 1806 |
| gtt ccc tgg cca tcg cct tgc cca tct cct tcc tct cgc cca cct tct<br>Val Pro Trp Pro Ser Pro Cys Pro Ser Pro Ser Ser Arg Pro Pro Ser<br>550 555 560 | 1854 |
| cgc tac cag tca ggt ccc aac tct ctt cca cct cgg gca gcc acc cct<br>Arg Tyr Gln Ser Gly Pro Asn Ser Leu Pro Pro Arg Ala Ala Thr Pro<br>565 570 575 580 | 1902 |
| aca cgg ccg ccc tcc agg ccc ccc tcg cgg cca tcc aga ccc ccg tct<br>Thr Arg Pro Pro Ser Arg Pro Pro Ser Arg Pro Ser Arg Pro Pro Ser<br>585 590 595 | 1950 |
| cac ccc tct gct cat ggt tct cca gct cct gtc tct act atg cct aaa<br>His Pro Ser Ala His Gly Ser Pro Ala Pro Val Ser Thr Met Pro Lys<br>600 605 610 | 1998 |
| cgc atg tct tca gaa ggg cct cca agg atg tcc cca aag gcc cag cga<br>Arg Met Ser Ser Glu Gly Pro Pro Arg Met Ser Pro Lys Ala Gln Arg<br>615 620 625 | 2046 |
| cat cct cga aat cac aga gtt tct gct ggg agg ggt tcc ata tcc agt<br>His Pro Arg Asn His Arg Val Ser Ala Gly Arg Gly Ser Ile Ser Ser<br>630 635 640 | 2094 |
| ggc cta gaa ttt gta tcc cac aac cca ccc agt gaa gca gct act cct<br>Gly Leu Glu Phe Val Ser His Asn Pro Pro Ser Glu Ala Ala Thr Pro<br>645 650 655 660 | 2142 |
| cca gta gca agg acc agt ccc tcg ggg gga acg tgg tca tca gtg gtc<br>Pro Val Ala Arg Thr Ser Pro Ser Gly Gly Thr Trp Ser Ser Val Val<br>665 670 675 | 2190 |
| agt ggg gtt cca aga tta tcc cct aaa act cat aga ccc agg tct ccc<br>Ser Gly Val Pro Arg Leu Ser Pro Lys Thr His Arg Pro Arg Ser Pro<br>680 685 690 | 2238 |
| aga cag aac agt att gga aat acc ccc agt ggg cca gtt ctt gct tct<br>Arg Gln Asn Ser Ile Gly Asn Thr Pro Ser Gly Pro Val Leu Ala Ser<br>695 700 705 | 2286 |
| ccc caa gct ggt att att cca act gaa gct gtt gcc atg cct att cca<br>Pro Gln Ala Gly Ile Ile Pro Thr Glu Ala Val Ala Met Pro Ile Pro<br>710 715 720 | 2334 |
| gct gca tct cct acg cct gct agt cct gca tcg aac aga gct gtt acc<br>Ala Ala Ser Pro Thr Pro Ala Ser Pro Ala Ser Asn Arg Ala Val Thr<br>725 730 735 740 | 2382 |
| cct tct agt gag gct aaa gat tcc agg ctt caa gat cag agg cag aac<br>Pro Ser Ser Glu Ala Lys Asp Ser Arg Leu Gln Asp Gln Arg Gln Asn | 2430 |

-continued

|  |  |  | 745 |  |  |  | 750 |  |  |  | 755 |  |  |  |  |
|---|---|---|---|---|---|---|---|---|---|---|---|---|---|---|---|
| tct | cct | gca | ggg | aat | aaa | gaa | aat | att | aaa | ccc | aat | gaa | aca | tca | cct | 2478 |
| Ser | Pro | Ala | Gly | Asn | Lys | Glu | Asn | Ile | Lys | Pro | Asn | Glu | Thr | Ser | Pro |
|  |  |  | 760 |  |  |  | 765 |  |  |  | 770 |  |  |  |  |

| agc | ttc | tca | aaa | gct | gaa | aac | aaa | ggt | ata | tca | cca | gtt | gtt | tct | gaa | 2526 |
| Ser | Phe | Ser | Lys | Ala | Glu | Asn | Lys | Gly | Ile | Ser | Pro | Val | Val | Ser | Glu |
|  |  |  | 775 |  |  |  | 780 |  |  |  | 785 |  |  |  |  |

| cat | aga | aaa | cag | att | gat | gat | tta | aag | aaa | ttt | aag | aat | gat | ttt | agg | 2574 |
| His | Arg | Lys | Gln | Ile | Asp | Asp | Leu | Lys | Lys | Phe | Lys | Asn | Asp | Phe | Arg |
|  |  |  | 790 |  |  |  | 795 |  |  |  | 800 |  |  |  |  |

| tta | cag | cca | agt | tct | act | tct | gaa | tct | atg | gat | caa | cta | cta | aac | aaa | 2622 |
| Leu | Gln | Pro | Ser | Ser | Thr | Ser | Glu | Ser | Met | Asp | Gln | Leu | Leu | Asn | Lys |
| 805 |  |  |  |  | 810 |  |  |  |  | 815 |  |  |  |  | 820 |

| aat | aga | gag | gga | gaa | aaa | tca | aga | gat | ttg | atc | aaa | gac | aaa | att | gaa | 2670 |
| Asn | Arg | Glu | Gly | Glu | Lys | Ser | Arg | Asp | Leu | Ile | Lys | Asp | Lys | Ile | Glu |
|  |  |  |  | 825 |  |  |  |  | 830 |  |  |  |  | 835 |  |

| cca | agt | gct | aag | gat | tct | ttc | att | gaa | aat | agc | agc | agc | aac | tgt | acc | 2718 |
| Pro | Ser | Ala | Lys | Asp | Ser | Phe | Ile | Glu | Asn | Ser | Ser | Ser | Asn | Cys | Thr |
|  |  |  |  | 840 |  |  |  |  | 845 |  |  |  |  | 850 |  |

| agt | ggc | agc | agc | aag | ccg | aat | agc | ccc | agc | att | tcc | cct | tca | ata | ctt | 2766 |
| Ser | Gly | Ser | Ser | Lys | Pro | Asn | Ser | Pro | Ser | Ile | Ser | Pro | Ser | Ile | Leu |
|  |  |  | 855 |  |  |  |  | 860 |  |  |  |  | 865 |  |  |

| agt | aac | acg | gag | cac | aag | agg | gga | cct | gag | gtc | act | tcc | caa | ggg | gtt | 2814 |
| Ser | Asn | Thr | Glu | His | Lys | Arg | Gly | Pro | Glu | Val | Thr | Ser | Gln | Gly | Val |
|  |  |  | 870 |  |  |  |  | 875 |  |  |  |  | 880 |  |  |

| cag | act | tcc | agc | cca | gca | tgt | aaa | caa | gag | aaa | gac | gat | aag | gaa | gag | 2862 |
| Gln | Thr | Ser | Ser | Pro | Ala | Cys | Lys | Gln | Glu | Lys | Asp | Asp | Lys | Glu | Glu |
| 885 |  |  |  |  | 890 |  |  |  |  | 895 |  |  |  |  | 900 |

| aag | aaa | gac | gca | gct | gag | caa | gtt | agg | aaa | tca | aca | ttg | aat | ccc | aat | 2910 |
| Lys | Lys | Asp | Ala | Ala | Glu | Gln | Val | Arg | Lys | Ser | Thr | Leu | Asn | Pro | Asn |
|  |  |  |  | 905 |  |  |  |  | 910 |  |  |  |  | 915 |  |

| gca | aag | gag | ttc | aac | cca | cgt | tcc | ttc | tct | cag | cca | aag | cct | tct | act | 2958 |
| Ala | Lys | Glu | Phe | Asn | Pro | Arg | Ser | Phe | Ser | Gln | Pro | Lys | Pro | Ser | Thr |
|  |  |  | 920 |  |  |  |  | 925 |  |  |  |  | 930 |  |  |

| acc | cca | act | tca | cct | cgg | cct | caa | gca | caa | cct | agc | cca | tct | atg | gtg | 3006 |
| Thr | Pro | Thr | Ser | Pro | Arg | Pro | Gln | Ala | Gln | Pro | Ser | Pro | Ser | Met | Val |
|  |  |  | 935 |  |  |  |  | 940 |  |  |  |  | 945 |  |  |

| ggt | cat | caa | cag | cca | act | cca | gtt | tat | act | cag | cct | gtt | tgt | ttt | gca | 3054 |
| Gly | His | Gln | Gln | Pro | Thr | Pro | Val | Tyr | Thr | Gln | Pro | Val | Cys | Phe | Ala |
|  |  |  | 950 |  |  |  |  | 955 |  |  |  |  | 960 |  |  |

| cca | aat | atg | atg | tat | cca | gtc | cca | gtg | agc | cca | ggc | gtg | caa | cct | tta | 3102 |
| Pro | Asn | Met | Met | Tyr | Pro | Val | Pro | Val | Ser | Pro | Gly | Val | Gln | Pro | Leu |
| 965 |  |  |  |  | 970 |  |  |  |  | 975 |  |  |  |  | 980 |

| tac | cca | ata | cct | atg | acg | ccc | atg | cca | gtg | aat | caa | gcc | aag | aca | tat | 3150 |
| Tyr | Pro | Ile | Pro | Met | Thr | Pro | Met | Pro | Val | Asn | Gln | Ala | Lys | Thr | Tyr |
|  |  |  |  | 985 |  |  |  |  | 990 |  |  |  |  | 995 |  |

| aga | gca | gta | cca | aat | atg | ccc | caa | cag | cgg | caa | gac | cag | cat | cat | cag | 3198 |
| Arg | Ala | Val | Pro | Asn | Met | Pro | Gln | Gln | Arg | Gln | Asp | Gln | His | His | Gln |
|  |  |  |  | 1000 |  |  |  |  | 1005 |  |  |  |  | 1010 |  |

| agt | gcc | atg | atg | cac | cca | gcg | tca | gca | gcg | ggc | cca | ccg | att | gca | gcc | 3246 |
| Ser | Ala | Met | Met | His | Pro | Ala | Ser | Ala | Ala | Gly | Pro | Pro | Ile | Ala | Ala |
|  |  |  |  | 1015 |  |  |  |  | 1020 |  |  |  |  | 1025 |  |

| acc | cca | cca | gct | tac | tcc | acg | caa | tat | gtt | gcc | tac | agt | cct | cag | cag | 3294 |
| Thr | Pro | Pro | Ala | Tyr | Ser | Thr | Gln | Tyr | Val | Ala | Tyr | Ser | Pro | Gln | Gln |
|  |  |  |  | 1030 |  |  |  |  | 1035 |  |  |  |  | 1040 |  |

| ttc | cca | aat | cag | ccc | ctt | gtt | cag | cat | gtg | cca | cat | tat | cag | tct | cag | 3342 |
| Phe | Pro | Asn | Gln | Pro | Leu | Val | Gln | His | Val | Pro | His | Tyr | Gln | Ser | Gln |
| 1045 |  |  |  |  | 1050 |  |  |  |  | 1055 |  |  |  |  | 1060 |

| cat | cct | cat | gtc | tat | agt | cct | gta | ata | cag | ggt | aat | gct | aga | atg | atg | 3390 |

```
                His Pro His Val Tyr Ser Pro Val Ile Gln Gly Asn Ala Arg Met Met
                            1065                1070                1075 gca cca cca aca cac gcc cag cct ggt tta gta tct tct tca gca act                  3438
Ala Pro Pro Thr His Ala Gln Pro Gly Leu Val Ser Ser Ser Ala Thr
    1080                1085                1090 cag tac ggg gct cat gag cag acg cat gcg atg tat gca tgt ccc aaa                  3486
Gln Tyr Gly Ala His Glu Gln Thr His Ala Met Tyr Ala Cys Pro Lys
1095                1100                1105 tta cca tac aac aag gag aca agc cct tct ttc tac ttt gcc att tcc                  3534
Leu Pro Tyr Asn Lys Glu Thr Ser Pro Ser Phe Tyr Phe Ala Ile Ser
    1110                1115                1120 acg ggc tcc ctt gct cag cag tat gcg cac cct aac gct acc ctg cac                  3582
Thr Gly Ser Leu Ala Gln Gln Tyr Ala His Pro Asn Ala Thr Leu His
1125                1130                1135                1140 cca cat act cca cac cct cag cct tca gct acc ccc act gga cag cag                  3630
Pro His Thr Pro His Pro Gln Pro Ser Ala Thr Pro Thr Gly Gln Gln
                1145                1150                1155 caa agc caa cat ggt gga agt cat cct gca ccc agt cct gtt cag cac                  3678
Gln Ser Gln His Gly Gly Ser His Pro Ala Pro Ser Pro Val Gln His
            1160                1165                1170 cat cag cac cag gcc gcc cag gct ctc cat ctg gcc agt cca cag cag                  3726
His Gln His Gln Ala Ala Gln Ala Leu His Leu Ala Ser Pro Gln Gln
        1175                1180                1185 cag tca gcc att tac cac gcg ggg ctt gcg cca act cca ccc tcc atg                  3774
Gln Ser Ala Ile Tyr His Ala Gly Leu Ala Pro Thr Pro Pro Ser Met
    1190                1195                1200 aca cct gcc tcc aac acg cag tcg cca cag aat agt ttc cca gca gca                  3822
Thr Pro Ala Ser Asn Thr Gln Ser Pro Gln Asn Ser Phe Pro Ala Ala
1205                1210                1215                1220 caa cag act gtc ttt acg atc cat cct tct cac gtt cag ccg gcg tat                  3870
Gln Gln Thr Val Phe Thr Ile His Pro Ser His Val Gln Pro Ala Tyr
                1225                1230                1235 acc aac cca ccc cac atg gcc cac gta cct cag gct cat gta cag tca                  3918
Thr Asn Pro Pro His Met Ala His Val Pro Gln Ala His Val Gln Ser
            1240                1245                1250 gga atg gtt cct tct cat cca act gcc cat gcg cca atg atg cta atg                  3966
Gly Met Val Pro Ser His Pro Thr Ala His Ala Pro Met Met Leu Met
        1255                1260                1265 acg aca cag cca ccc ggc ggt ccc cag gcc gcc ctc gct caa agt gca                  4014
Thr Thr Gln Pro Pro Gly Gly Pro Gln Ala Ala Leu Ala Gln Ser Ala
    1270                1275                1280 cta cag ccc att cca gtc tcg aca aca gcg cat ttc ccc tat atg acg                  4062
Leu Gln Pro Ile Pro Val Ser Thr Thr Ala His Phe Pro Tyr Met Thr
1285                1290                1295                1300 cac cct tca gta caa gcc cac cac caa cag cag ttg t aaggctgccc                     4109
His Pro Ser Val Gln Ala His His Gln Gln Gln Leu
                1305                1310 tggaggaacc gaaaggccaa attccctcct cccttctact gcttctacca actggaagca                4169
cagaaaacta gaatttcatt tattttgttt ttaaaatata tatgttgatt tcttgtaaca                4229
tccaatagga atgctaacag ttcacttgca gtggaagata cttggaccga gtagaggcat                4289
ttaggaactt gggggctatt ccataattcc atatgctgtt tcagagtccc gcaggtaccc                4349
cagctctgct tgccgaaact ggaagttatt tattttttaa taaccettga agtcatgaa                 4409 cacatcagct agcaaaagaa gtaacaagag tgattcttgc tgctattact gctaaaaaaa                4469
aaaaaaaaaa aa                                                                    4481
```

<210> SEQ ID NO 2

-continued

```
<211> LENGTH: 1312
<212> TYPE: PRT
<213> ORGANISM: Homo sapien

<400> SEQUENCE: 2

Met Arg Ser Ala Ala Ala Pro Arg Ser Pro Ala Val Ala Thr Glu
 1               5                  10                  15

Ser Arg Arg Phe Ala Ala Arg Trp Pro Gly Trp Arg Ser Leu Gln
                20                  25                  30

Arg Pro Ala Arg Arg Ser Gly Arg Gly Gly Gly Ala Ala Pro Gly
                35                  40                  45

Pro Tyr Pro Ser Ala Ala Pro Pro Pro Gly Pro Gly Pro Pro Pro
            50                  55                  60

Ser Arg Gln Ser Ser Pro Ser Ala Ser Asp Cys Phe Gly Ser Asn
65                  70                  75                  80

Gly Asn Gly Gly Gly Ala Phe Arg Pro Gly Ser Arg Arg Leu Leu Gly
                    85                  90                  95

Leu Gly Gly Pro Pro Arg Pro Phe Val Val Val Leu Pro Leu Ala
                100                 105                 110

Ser Pro Gly Ala Pro Pro Ala Ala Pro Thr Arg Ala Ser Pro Leu Gly
                115                 120                 125

Ala Arg Ala Ser Pro Pro Arg Ser Gly Val Ser Leu Ala Arg Pro Ala
            130                 135                 140

Pro Gly Cys Pro Arg Pro Ala Cys Glu Pro Val Tyr Gly Pro Leu Thr
145                 150                 155                 160

Met Ser Leu Lys Pro Gln Gln Gln Gln Gln Gln Gln Gln Gln
                165                 170                 175

Gln Gln Gln Gln Gln Gln Gln Gln Gln Pro Pro Ala Ala
                180                 185                 190

Ala Asn Val Arg Lys Pro Gly Gly Ser Gly Leu Leu Ala Ser Pro Ala
                195                 200                 205

Ala Ala Pro Ser Pro Ser Ser Ser Val Ser Ser Ser Ala Thr
            210                 215                 220

Ala Pro Ser Ser Val Val Ala Ala Thr Ser Gly Gly Arg Pro Gly
225                 230                 235                 240

Leu Gly Arg Gly Arg Asn Ser Asn Lys Gly Leu Pro Gln Ser Thr Ile
                245                 250                 255

Ser Phe Asp Gly Ile Tyr Ala Asn Met Arg Met Val His Ile Leu Thr
                260                 265                 270

Ser Val Val Gly Ser Lys Cys Glu Val Gln Val Lys Asn Gly Gly Ile
                275                 280                 285

Tyr Glu Gly Val Phe Lys Thr Tyr Ser Pro Lys Cys Asp Leu Val Leu
                290                 295                 300

Asp Ala Ala His Glu Lys Ser Thr Glu Ser Ser Ser Gly Pro Lys Arg
305                 310                 315                 320

Glu Glu Ile Met Glu Ser Ile Leu Phe Lys Cys Ser Asp Phe Val Val
                325                 330                 335

Val Gln Phe Lys Asp Met Asp Ser Ser Tyr Ala Lys Arg Asp Ala Phe
                340                 345                 350

Thr Asp Ser Ala Ile Ser Ala Lys Val Asn Gly Glu His Lys Glu Lys
                355                 360                 365

Asp Leu Glu Pro Trp Asp Ala Gly Glu Leu Thr Ala Asn Glu Glu Leu
                370                 375                 380

Glu Ala Leu Glu Asn Asp Val Ser Asn Gly Trp Asp Pro Asn Asp Met
```

```
385                 390                 395                 400

Phe Arg Tyr Asn Glu Asn Tyr Gly Val Val Ser Thr Tyr Asp Ser
                405                 410                 415

Ser Leu Ser Ser Tyr Thr Val Pro Leu Glu Arg Asp Asn Ser Glu Glu
                420                 425                 430

Phe Leu Lys Arg Glu Ala Arg Ala Asn Gln Leu Ala Glu Glu Ile Glu
                435                 440                 445

Ser Ser Ala Gln Tyr Lys Ala Arg Val Ala Leu Glu Asn Asp Asp Arg
450                 455                 460

Ser Glu Glu Glu Lys Tyr Thr Ala Val Gln Arg Asn Ser Ser Glu Arg
465                 470                 475                 480

Glu Gly His Ser Ile Asn Thr Arg Glu Asn Lys Tyr Ile Pro Pro Gly
                485                 490                 495

Gln Arg Asn Arg Glu Val Ile Ser Trp Gly Ser Gly Arg Gln Asn Ser
                500                 505                 510

Pro Arg Met Gly Gln Pro Gly Ser Gly Ser Met Pro Ser Arg Ser Thr
                515                 520                 525

Ser His Thr Ser Asp Phe Asn Pro Asn Ser Gly Ser Asp Gln Arg Val
                530                 535                 540

Val Asn Gly Gly Val Pro Trp Pro Ser Pro Cys Pro Ser Pro Ser Ser
545                 550                 555                 560

Arg Pro Pro Ser Arg Tyr Gln Ser Gly Pro Asn Ser Leu Pro Pro Arg
                565                 570                 575

Ala Ala Thr Pro Thr Arg Pro Pro Ser Arg Pro Ser Arg Pro Ser
                580                 585                 590

Arg Pro Pro Ser His Pro Ser Ala His Gly Ser Pro Ala Pro Val Ser
                595                 600                 605

Thr Met Pro Lys Arg Met Ser Ser Glu Gly Pro Pro Arg Met Ser Pro
                610                 615                 620

Lys Ala Gln Arg His Pro Arg Asn His Arg Val Ser Ala Gly Arg Gly
625                 630                 635                 640

Ser Ile Ser Ser Gly Leu Glu Phe Val Ser His Asn Pro Pro Ser Glu
                645                 650                 655

Ala Ala Thr Pro Pro Val Ala Arg Thr Ser Pro Ser Gly Gly Thr Trp
                660                 665                 670

Ser Ser Val Val Ser Gly Val Pro Arg Leu Ser Pro Lys Thr His Arg
                675                 680                 685

Pro Arg Ser Pro Arg Gln Asn Ser Ile Gly Asn Thr Pro Ser Gly Pro
                690                 695                 700

Val Leu Ala Ser Pro Gln Ala Gly Ile Ile Pro Thr Glu Ala Val Ala
705                 710                 715                 720

Met Pro Ile Pro Ala Ala Ser Pro Thr Pro Ala Ser Pro Ala Ser Asn
                725                 730                 735

Arg Ala Val Thr Pro Ser Ser Glu Ala Lys Asp Ser Arg Leu Gln Asp
                740                 745                 750

Gln Arg Gln Asn Ser Pro Ala Gly Asn Lys Glu Asn Ile Lys Pro Asn
                755                 760                 765

Glu Thr Ser Pro Ser Phe Ser Lys Ala Glu Asn Lys Gly Ile Ser Pro
                770                 775                 780

Val Val Ser Glu His Arg Lys Gln Ile Asp Asp Leu Lys Lys Phe Lys
785                 790                 795                 800

Asn Asp Phe Arg Leu Gln Pro Ser Ser Thr Ser Glu Ser Met Asp Gln
                805                 810                 815
```

-continued

```
Leu Leu Asn Lys Asn Arg Glu Gly Glu Lys Ser Arg Asp Leu Ile Lys
            820                 825                 830

Asp Lys Ile Glu Pro Ser Ala Lys Asp Ser Phe Ile Glu Asn Ser Ser
        835                 840                 845

Ser Asn Cys Thr Ser Gly Ser Ser Lys Pro Asn Ser Pro Ser Ile Ser
    850                 855                 860

Pro Ser Ile Leu Ser Asn Thr Glu His Lys Arg Gly Pro Glu Val Thr
865                 870                 875                 880

Ser Gln Gly Val Gln Thr Ser Ser Pro Ala Cys Lys Gln Glu Lys Asp
                885                 890                 895

Asp Lys Glu Glu Lys Lys Asp Ala Ala Glu Gln Val Arg Lys Ser Thr
            900                 905                 910

Leu Asn Pro Asn Ala Lys Glu Phe Asn Pro Arg Ser Phe Ser Gln Pro
        915                 920                 925

Lys Pro Ser Thr Thr Pro Thr Ser Pro Arg Pro Gln Ala Gln Pro Ser
    930                 935                 940

Pro Ser Met Val Gly His Gln Gln Pro Thr Pro Val Tyr Thr Gln Pro
945                 950                 955                 960

Val Cys Phe Ala Pro Asn Met Met Tyr Pro Val Pro Val Ser Pro Gly
                965                 970                 975

Val Gln Pro Leu Tyr Pro Ile Pro Met Thr Pro Met Pro Val Asn Gln
            980                 985                 990

Ala Lys Thr Tyr Arg Ala Val Pro Asn Met Pro Gln Gln Arg Gln Asp
        995                 1000                1005

Gln His His Gln Ser Ala Met Met His Pro Ala Ser Ala Ala Gly Pro
    1010                1015                1020

Pro Ile Ala Ala Thr Pro Pro Ala Tyr Ser Thr Gln Tyr Val Ala Tyr
1025                1030                1035                1040

Ser Pro Gln Gln Phe Pro Asn Gln Pro Leu Val Gln His Val Pro His
                1045                1050                1055

Tyr Gln Ser Gln His Pro His Val Tyr Ser Pro Val Ile Gln Gly Asn
            1060                1065                1070

Ala Arg Met Met Ala Pro Pro Thr His Ala Gln Pro Gly Leu Val Ser
        1075                1080                1085

Ser Ser Ala Thr Gln Tyr Gly Ala His Glu Gln Thr His Ala Met Tyr
    1090                1095                1100

Ala Cys Pro Lys Leu Pro Tyr Asn Lys Glu Thr Ser Pro Ser Phe Tyr
1105                1110                1115                1120

Phe Ala Ile Ser Thr Gly Ser Leu Ala Gln Gln Tyr Ala His Pro Asn
                1125                1130                1135

Ala Thr Leu His Pro His Thr Pro His Pro Gln Pro Ser Ala Thr Pro
            1140                1145                1150

Thr Gly Gln Gln Gln Ser Gln His Gly Gly Ser His Pro Ala Pro Ser
        1155                1160                1165

Pro Val Gln His His Gln His Gln Ala Ala Gln Ala Leu His Leu Ala
    1170                1175                1180

Ser Pro Gln Gln Gln Ser Ala Ile Tyr His Ala Gly Leu Ala Pro Thr
1185                1190                1195                1200

Pro Pro Ser Met Thr Pro Ala Ser Asn Thr Gln Ser Pro Gln Asn Ser
                1205                1210                1215

Phe Pro Ala Ala Gln Gln Thr Val Phe Thr Ile His Pro Ser His Val
            1220                1225                1230
```

-continued

```
Gln Pro Ala Tyr Thr Asn Pro Pro His Met Ala His Val Pro Gln Ala
        1235                1240                1245

His Val Gln Ser Gly Met Val Pro Ser His Pro Thr Ala His Ala Pro
    1250                1255                1260

Met Met Leu Met Thr Thr Gln Pro Pro Gly Gly Pro Gln Ala Ala Leu
1265                1270                1275                1280

Ala Gln Ser Ala Leu Gln Pro Ile Pro Val Ser Thr Thr Ala His Phe
            1285                1290                1295

Pro Tyr Met Thr His Pro Ser Val Gln Ala His His Gln Gln Gln Leu
        1300                1305                1310

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 3
gcgtgcgagc cggtgtat                                                 18

<210> SEQ ID NO 4
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 4
cgggcttgcg gacattg                                                  17

<210> SEQ ID NO 5
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 5
ggttccttct catccaactg                                               20

<210> SEQ ID NO 6
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 6
gatgtgttca tgactttcaa gg                                            22

<210> SEQ ID NO 7
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 7
ttacagccaa gtctactctg aa                                            22

<210> SEQ ID NO 8
<211> LENGTH: 19
<212> TYPE: DNA
```

-continued

```
<213> ORGANISM: Artificial Sequence
<220> FEATURE:
<223> OTHER INFORMATION: synthetic oligonucleotide

<400> SEQUENCE: 8
agtctgaacc ccttgggaa                                              19

<210> SEQ ID NO 9
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 9
gggcccctca ccatgtcg                                               18

<210> SEQ ID NO 10
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 10
cgggcttgcg gacattgg                                               18

<210> SEQ ID NO 11
<211> LENGTH: 1257
<212> TYPE: DNA
<213> ORGANISM: mus musculus
<220> FEATURE:
<221> NAME/KEY: CDS
<222> LOCATION: (2)...(1257)

<400> SEQUENCE: 11 g cac gag ggg ccg ctc acc atg tcg ctg aag ccg cag ccg cag ccg ccc      49
  His Glu Gly Pro Leu Thr Met Ser Leu Lys Pro Gln Pro Gln Pro Pro
    1               5                  10                  15 gcg ccc gcc act ggc cgc aag ccc ggc ggc ggc ctg ctc tcg tcg ccc        97
Ala Pro Ala Thr Gly Arg Lys Pro Gly Gly Gly Leu Leu Ser Ser Pro
             20                  25                  30 ggc gcc gcg ccg gcc tcg gcc gcg gtg acc tcg gct tcc gtg gtg ccg       145
Gly Ala Ala Pro Ala Ser Ala Ala Val Thr Ser Ala Ser Val Val Pro
         35                  40                  45 gcc ccg gcc gcg ccg gtg gcg tct tcc tcg gcg gcc gcg ggc ggc ggg       193
Ala Pro Ala Ala Pro Val Ala Ser Ser Ser Ala Ala Ala Gly Gly Gly
     50                  55                  60 cgt ccc ggc ctg ggc aga ggt cgg aac agt agc aaa gga ctg cct cag       241
Arg Pro Gly Leu Gly Arg Gly Arg Asn Ser Ser Lys Gly Leu Pro Gln
 65                  70                  75                  80 cct acg att tct ttt gat gga atc tat gca aac gtg agg atg gtt cat       289
Pro Thr Ile Ser Phe Asp Gly Ile Tyr Ala Asn Val Arg Met Val His
                 85                  90                  95 ata ctt acg tca gtt gtt gga tcg aaa tgt gaa gta caa gtg aaa aac       337
Ile Leu Thr Ser Val Val Gly Ser Lys Cys Glu Val Gln Val Lys Asn
            100                 105                 110 gga ggc ata tat gaa gga gtt ttt aaa aca tac agt cct aag tgt gac       385
Gly Gly Ile Tyr Glu Gly Val Phe Lys Thr Tyr Ser Pro Lys Cys Asp
        115                 120                 125 ttg gta ctt gat gct gca cat gag aaa agt aca gaa tcc agt tcg ggg       433
Leu Val Leu Asp Ala Ala His Glu Lys Ser Thr Glu Ser Ser Ser Gly
    130                 135                 140
```

```
cca aaa cgt gaa gaa ata atg gag agt gtt ttg ttc aaa tgc tca gac       481
Pro Lys Arg Glu Glu Ile Met Glu Ser Val Leu Phe Lys Cys Ser Asp
145                 150                 155                 160 ttc gtt gtg gta cag ttt aaa gat aca gac tcc agt tat gca cgg aga       529
Phe Val Val Val Gln Phe Lys Asp Thr Asp Ser Ser Tyr Ala Arg Arg
                165                 170                 175 gat gct ttt act gac tct gct ctc agc gca aag gtg aat ggt gag cac       577
Asp Ala Phe Thr Asp Ser Ala Leu Ser Ala Lys Val Asn Gly Glu His
        180                 185                 190 aag gag aag gac ctg gag ccc tgg gat gca ggg gag ctc acg gcc agc       625
Lys Glu Lys Asp Leu Glu Pro Trp Asp Ala Gly Glu Leu Thr Ala Ser
            195                 200                 205 gag gag ctg gag ctg gag aat gat gtg tct aat gga tgg gac ccc aat       673
Glu Glu Leu Glu Leu Glu Asn Asp Val Ser Asn Gly Trp Asp Pro Asn
210                 215                 220 gac atg ttt cga tat aat gaa gag aat tat ggt gtg gtg tcc aca tat       721
Asp Met Phe Arg Tyr Asn Glu Glu Asn Tyr Gly Val Val Ser Thr Tyr
225                 230                 235                 240 gat agc agt tta tct tca tat acg gtt cct tta gaa agg gac aac tca       769
Asp Ser Ser Leu Ser Ser Tyr Thr Val Pro Leu Glu Arg Asp Asn Ser
                245                 250                 255 gaa gaa ttt ctt aaa cgg gag gca agg gca aac cag tta gca gaa gaa       817
Glu Glu Phe Leu Lys Arg Glu Ala Arg Ala Asn Gln Leu Ala Glu Glu
            260                 265                 270 att gaa tcc agt gct cag tac aaa gct cgt gtc gcc ctt gag aat gat       865
Ile Glu Ser Ser Ala Gln Tyr Lys Ala Arg Val Ala Leu Glu Asn Asp
        275                 280                 285 gac cgg agt gag gaa gaa aaa tac aca gca gtc cag aga aac tgc agt       913
Asp Arg Ser Glu Glu Glu Lys Tyr Thr Ala Val Gln Arg Asn Cys Ser
290                 295                 300 gac cgg gag ggg cat ggc ccc aac act agg gac aat aaa tat att cct       961
Asp Arg Glu Gly His Gly Pro Asn Thr Arg Asp Asn Lys Tyr Ile Pro
305                 310                 315                 320 cct gga caa aga aac aga gaa gtc cta tcc tgg gga agt ggg aga cag      1009
Pro Gly Gln Arg Asn Arg Glu Val Leu Ser Trp Gly Ser Gly Arg Gln
                325                 330                 335 agc tca cca cgg atg ggc cag cct ggg cca ggc tcc atg ccg tca aga      1057
Ser Ser Pro Arg Met Gly Gln Pro Gly Pro Gly Ser Met Pro Ser Arg
            340                 345                 350 gct gct tct cac act tca gat ttc aac ccg aac gct ggc tca gac caa      1105
Ala Ala Ser His Thr Ser Asp Phe Asn Pro Asn Ala Gly Ser Asp Gln
        355                 360                 365 aga gta gtt aat gga ggt gtt ccc tgg cca tcg cct tgc cca tct cct      1153
Arg Val Val Asn Gly Gly Val Pro Trp Pro Ser Pro Cys Pro Ser Pro
370                 375                 380 tcc tct cgc cca cct tct cgc tac cag tca ggt ccc aac tct ctt cca      1201
Ser Ser Arg Pro Pro Ser Arg Tyr Gln Ser Gly Pro Asn Ser Leu Pro
385                 390                 395                 400 cct cgg gca gcc acc cct aca cgg cct cgt gcc gaa ttc ctg cag ccc      1249
Pro Arg Ala Ala Thr Pro Thr Arg Pro Arg Ala Glu Phe Leu Gln Pro
                405                 410                 415 ggg gat cc                                                            1257
Gly Asp <210> SEQ ID NO 12
<211> LENGTH: 418
<212> TYPE: PRT
<213> ORGANISM: mus musculus

<400> SEQUENCE: 12
```

-continued

```
His Gln Gly Pro Leu Thr Met Ser Leu Lys Pro Gln Pro Gln Pro Pro
  1               5                   10                  15

Ala Pro Ala Thr Gly Arg Lys Pro Gly Gly Leu Leu Ser Ser Pro
              20                  25                  30

Gly Ala Ala Pro Ala Ser Ala Val Thr Ser Ala Ser Val Val Pro
              35                  40                  45

Ala Pro Ala Ala Pro Val Ala Ser Ser Ala Ala Ala Gly Gly Gly
 50                  55                  60

Arg Pro Gly Leu Gly Arg Gly Arg Asn Ser Ser Lys Gly Leu Pro Gln
 65                  70                  75                  80

Pro Thr Ile Ser Phe Asp Gly Ile Tyr Ala Asn Val Arg Met Val His
                     85                  90                  95

Ile Leu Thr Ser Val Val Gly Ser Lys Cys Glu Val Gln Val Lys Asn
              100                 105                 110

Gly Gly Ile Tyr Glu Gly Val Phe Lys Thr Tyr Ser Pro Lys Cys Asp
              115                 120                 125

Leu Val Leu Asp Ala Ala His Glu Lys Ser Thr Glu Ser Ser Ser Gly
 130                 135                 140

Pro Lys Arg Glu Glu Ile Met Glu Ser Val Leu Phe Lys Cys Ser Asp
145                 150                 155                 160

Phe Val Val Val Gln Phe Lys Asp Thr Asp Ser Ser Tyr Ala Arg Arg
                 165                 170                 175

Asp Ala Phe Thr Asp Ser Ala Leu Ser Ala Lys Val Asn Gly Glu His
             180                 185                 190

Lys Glu Lys Asp Leu Glu Pro Trp Asp Ala Gly Glu Leu Thr Ala Ser
             195                 200                 205

Glu Glu Leu Glu Leu Glu Asn Asp Val Ser Asn Gly Trp Asp Pro Asn
210                 215                 220

Asp Met Phe Arg Tyr Asn Glu Glu Asn Tyr Gly Val Val Ser Thr Tyr
225                 230                 235                 240

Asp Ser Ser Leu Ser Ser Tyr Thr Val Pro Leu Glu Arg Asp Asn Ser
                 245                 250                 255

Glu Glu Phe Leu Lys Arg Glu Ala Arg Ala Asn Gln Leu Ala Glu Glu
             260                 265                 270

Ile Glu Ser Ser Ala Gln Tyr Lys Ala Arg Val Ala Leu Glu Asn Asp
             275                 280                 285

Asp Arg Ser Glu Glu Glu Lys Tyr Thr Ala Val Gln Arg Asn Cys Ser
290                 295                 300

Asp Arg Glu Gly His Gly Pro Asn Thr Arg Asp Asn Lys Tyr Ile Pro
305                 310                 315                 320

Pro Gly Gln Arg Asn Arg Glu Val Leu Ser Trp Gly Ser Gly Arg Gln
                 325                 330                 335

Ser Ser Pro Arg Met Gly Gln Pro Gly Pro Gly Ser Met Pro Ser Arg
             340                 345                 350

Ala Ala Ser His Thr Ser Asp Phe Asn Pro Asn Ala Gly Ser Asp Gln
             355                 360                 365

Arg Val Val Asn Gly Gly Val Pro Trp Pro Ser Pro Cys Pro Ser Pro
370                 375                 380
```

```
Ser Ser Arg Pro Pro Ser Arg Tyr Gln Ser Gly Pro Asn Ser Leu Pro
385                 390                 395                 400

Pro Arg Ala Ala Thr Pro Thr Arg Pro Arg Ala Glu Phe Leu Gln Pro
            405                 410                 415

Gly Asp
```